(12) United States Patent
Kaneda et al.

(10) Patent No.: US 7,304,726 B2
(45) Date of Patent: Dec. 4, 2007

(54) AUTO DISTINCTION SYSTEM

(75) Inventors: Hiroshi Kaneda, Himeji (JP); Masaki Takebe, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 93 days.

(21) Appl. No.: 10/557,558

(22) PCT Filed: May 17, 2004

(86) PCT No.: PCT/JP2004/006626

§ 371 (c)(1),
(2), (4) Date: Nov. 21, 2005

(87) PCT Pub. No.: WO2004/104290

PCT Pub. Date: Dec. 2, 2004

(65) Prior Publication Data

US 2007/0064999 A1    Mar. 22, 2007

(30) Foreign Application Priority Data

May 21, 2003   (JP) ............................. 2003-143794

(51) Int. Cl.
*G01N 21/00* (2006.01)
(52) U.S. Cl. ..................................... 356/73.1
(58) Field of Classification Search ............... None
See application file for complete search history.

(56) References Cited

U.S. PATENT DOCUMENTS 5,223,715 A * 6/1993 Taylor ..................... 250/343
6,587,189 B1 * 7/2003 Roberts et al. ............ 356/73.1
6,734,958 B1 * 5/2004 MacKinnon et al. ....... 356/236

FOREIGN PATENT DOCUMENTS

| JP | 61-195332 A | 8/1986 |
|----|-------------|--------|
| JP | 2-274194 A  | 11/1990 |
| JP | 5-509136 A  | 12/1993 |
| JP | 6-258231 A  | 9/1994 |
| JP | 8-122269 A  | 5/1996 |
| JP | 8-145905 A  | 6/1996 |
| JP | 8-158221 A  | 6/1996 |
| JP | 2002-236004 A | 8/2002 |
| WO | WO-92/02001 A1 | 2/1992 |

\* cited by examiner

Primary Examiner—Tu T. Nguyen
(74) Attorney, Agent, or Firm—Birch, Stewart, Kolasch & Birch, LLP

(57) ABSTRACT

An auto distinction system images an assembled fiber band which continuously moves on the front side of a background plate applies sync-separating to a video signal by a sync-separating circuit 5a, and clamps the video signal by a clamping circuit 5b. Based on the clamped image signal, the characteristic information containing the defect information of the assembled fiber band is detected, and the defect information is extracted from the detected characteristic information. The clamped image signal is supplied to a noise-eliminating circuit 6a and a defect signal concerning the thickness of the assembled fiber band is extracted. Based on the extracted signal and a reference signal with respect to the information, suitability of the defect information is discriminated by a distinction circuit 7. When the results of distinction are defective, the results are announced. The characteristic information can be used for process control by being supplied to an external computer.

22 Claims, 14 Drawing Sheets

AUTO DISTINCTION SYSTEM

BACKGROUND OF THE INVENTION

1. Field of the Invention

The present invention relates to an auto distinction system which detects a characteristic information including a defect information of a continuously moving assembled fiber band (for example, a fiber bundle or fiber assembly such as filter tow) and which is useful for quality control of the assembled fiber band on the basis of the defect information or time sequence (TSEQ) fluctuation information; and relates to an auto distinction method.

2. Description of the Related Art

A video signal from an imaging means is used for quality control and discriminating whether an inspection target is non-defective or defective. For example, the specification of Japanese Patent No. 3013903 discloses a defect-sensing device for detecting a defect of an edge of a flat glass having chamfered edges and seaming surfaces, in which the device detects on the edge of glass placed horizontally; wherein the device comprises a light source for irradiating the edge with light from upper diagonal and lower diagonal directions opposite side of the flat glass, and at least two cameras which are disposed outside of the extended ranges of light paths irradiated onto the glass edge; and the device images the edge via transparent portions of the flat glass from opposite sides of the light irradiation directions. The defect-sensing device finds a weathering or burn-in defect based on the level of a brightness signal of an image signal picked up by the cameras. However, this device requires a plurality of light sources and a plurality of imaging means.

The specification of Japanese Patent No. 3025833 discloses an inspection system comprising a signal pattern generating unit, a threshold pattern generating means, and a comparing means. The generating unit generates at least one signal pattern selected from (a) a signal pattern where a maximum value is offset to become higher by an offset value in the video signal pattern and (b) a signal pattern where a minimum value is offset to become lower by an offset value in the video signal pattern, wherein the video signal patterns are obtained by imaging a non-defective product with an imaging means. The threshold pattern generating means generates threshold patterns from the offset signal patterns. The comparing means discriminates quality (or good or bad) of an inspection target by comparing a video signal obtained by imaging the inspection target with threshold patterns. The Japanese Patent Application Laid-open No. 122269/1996 (JP-A-H8-122269) discloses an image pickup type inspection system comprising an imaging means which outputs a video signal by imaging an inspection target, an inspection region setting means for setting an inspection region in the imaged field through the imaging means, an abnormal portion detecting means for detecting an abnormal portion on the basis of the video signal within the inspection region, and a non-defective/defective distinction signal output means for outputting a non-defective/defective distinction signal according to whether or not an abnormal portion has been detected, wherein these means are housed in one casing. This document also mentions that the image pickup type inspection system further comprises an announcing means for announcing the results of non-defective/defective distinction to the outside by means of light or sound.

However, when these systems are applied to an assembled fiber band which continuously moves, it becomes difficult to accurately detect defects such as stains and unevenness of thick or thin portions, because not only does an inspection target continuously move, but also the width and thickness of the assembled fiber band fluctuate by continuous moving. In particular, when the systems are applied to a fiber bundle such as filter tow which comprises a plurality of yarns and moves at a high speed, not only does the degree of adjacency or overlapping of yarns fluctuates, but also these fluctuations further change every moment as the yarns move. Accordingly it becomes difficult to accurately detect defects (or uneven portions) of the assembled fiber band or fiber pieces.

Therefore, an object of the present invention is to provide an auto distinction system which is distinctable suitability of the assembled fiber band by accurately extracting defective portions or uneven portions of the assembled fiber band (or fiber assembly) even when the assembled fiber band continuously moves; and an auto distinction method thereof.

Another object of the present invention is to provide an auto distinction system which is distinctable suitability of an assembled fiber band by extracting or detecting a defect information (or a characteristic information including at least a defect information) concerning at least two characteristics selected from a width, a thickness, and a stain of the assembled fiber band; and an auto distinction method thereof.

Still another object of the present invention is to provide a system which efficiently detects fluctuations in a width, a thickness and a stain of an assembled fiber band even when the assembled fiber band is a band-shaped assembled fiber band such as filter tow which moves or runs at a high speed, and a method thereof.

Still another object of the present invention is to provide an auto distinction system useful for process control and quality control at a production site, wherein a characteristic information of an assembled fiber band is accurately detected by the system even when the assembled fiber band continuously moves, and further the characteristic information (detection signal and/or data) is transferred to a computer (for example, a process controlling computer) and used as a time sequence fluctuation information (time-series fluctuation information); and an auto distinction method thereof.

Patent Document 1: Specification of Patent Document No. 3013903

Patent Document 2: Specification of Patent Document No. 3025833

Patent Document 3: Japanese Patent Application Laid-open No. 122269/1996 (JP-A-H8-122269)

SUMMARY OF THE INVENTION

The inventors of the present invention conducted intensive investigation to accomplish the above objects, and finally found that, when (1) an assembled fiber band which continuously moves (or runs) is imaged by an imaging means and (2) a video signal from the imaging means is subjected to sync-separating and clamping, (3) on the basis of the clamped image signal (clamped image signal), a characteristic information including a defect information on the width, thickness and/or stain of the assembled fiber band is detected by a detecting means, and (4) the defect information is extracted from the characteristic information by an extracting means, (a) suitability of the assembled fiber band is accurately distinctablie or can be properly discriminated by comparison with reference values with respect to the above information, (b) by using scanning lines with respect to the width, thickness, andlor stain of the assembled fiber band, the plurality of characteristics could be efficiently and accurately discriminated, and (c) use of time sequence or time-series fluctuations of the characteristic information was effective for process control and quality control. The present invention was accomplished based on the above finding.

That is, the auto distinction system of the present invention comprises an imaging means (image pick up means) for imaging an assembled fiber band (arrayed fiber body or fiber assembly) which continuously moves, a sync-separating and clamping means for sync-separating and clamping a video signal from this imaging means, a detecting means for detecting a characteristic information including a defect information with respect to at least one characteristic selected from a width, a thickness, and a stain (refers to a defective or abnormal portion in some cases) of the assembled fiber band on the basis of the clamped image signal from this sync-separating and clamping means, an extracting means for extracting the defect information from the characteristic information detected by the detecting means, and a distinction means for discriminating suitability of the defect information on the basis of both the extracted signal from this extracting means and a reference signal with respect to the information (detected characteristic information or defect information). In this system, the characteristic information may be detected and the defect information may be extracted by using a luminance signal in the video signal. Namely, the sync-separating and clamping means (sync-separating/clamping means) may sync-separate and clamp a luminance signal in the video signal. In the above-mentioned system, since the video signal is subjected to sync-separating and clamping, the standard level can be fixed. Accordingly, the defect information with respect to the width, the thickness, and the stain of the assembled fiber band can be efficiently detected. Further, suitability of the assembled fiber band is accurately distinctable or capable of discriminated. Incidentally, with respect to sync-separating and clamping of the video signal, a synchronizing signal may be separated from a video signal by a sync-separating means, and in response to the synchronizing signal from the sync-separating means, the video signal may be clamped by the clamp means.

In order to increase imaging contrast of the assembled fiber band by the imaging means as well as to enhance the accuracy of detection of the defective portion, the above-mentioned system may have an illuminating means that is disposed outside of a visual field (out-of-view) of the imaging means and is for illuminating the assembled fiber band, and a background plate for forming the background of the assembled fiber band for the illuminating means. This background plate may have a high contrast color to the assembled fiber band, or may have a color similar to that of the assembled fiber band, or a low contrast color (or substantially the same contrast color with that of the assembled fiber band). When the background plate has a high contrast color in comparison with the assembled fiber band, the extracting means can extract a defect information on at least one characteristic selected from a width and a thickness of the assembled fiber band by using scanning lines of a video signal obtained by scanning the region having the high contrast color. On the other hand, when the background plate has a color similar to that of the assembled fiber band or has a low contrast color in comparison with the assembled fiber band, the extracting means can extract a defect information on at least one characteristic between a stain and a thickness of the assembled fiber band by using scanning lines of a video signal obtained by scanning the similar color region. A thickness fluctuation (or defect information) of the assembled fiber band can be detected in both cases of low contrast and high contrast colors of the background plate as long as the background plate color is even.

Incidentally, the assembled fiber band may be a band-shaped or ribbon shaped assembled fiber band (band-shaped tow band) comprising a plurality of yarns (or strands), for example, a plurality of yarns which are bundled and adjacently arrayed each other, or may be a band-shaped assembled fiber band (for example, filter tow (cigarette filter tow)) which comprises a plurality of yarns bundled, adjacently arrayed each other, and overlapped into a plurality of layers. Furthermore, the assembled fiber band may be usually an assembled fiber band through which a light ray transmits, or may be openable. Incidentally, as long as the illumination means exists out of visual field (out-of-view field) of the imaging means, the illuminating means may illuminate the assembled fiber band from the front side and/or the back side of the assembled fiber band, or the illuminating means may illuminate the assembled fiber band by transmitting a light beam through the assembled fiber band. The present invention is useful for extracting the characteristic information including a defect information on at least one characteristic selected from a width, a thickness, and a stain of a non-crimped or crimped band-shaped filter tow which continuously moves and comprises a plurality of yarns.

Furthermore, by the extracting means, the defect information on one or single characteristic may be detected, or the defect information on at least two characteristics selected from the width, the thickness, and the stain of the assembled fiber band may be extracted. In the case of extracting the defect information on a plurality of characteristics, the background plate may have a width larger than the width of the moving assembled fiber band, and may have a region having a color similar or low-contrast to in comparison with the inspection target. Further, the background plate may form high contrast zones for detecting the width of the assembled fiber band in the direction across the moving direction of the assembled fiber band. Such a background plate ensures to obtain an information on a defective portion with respect to the width of an inspection target by using the scanning lines of the video signal obtained by scanning the high contrast zones in the imaging field of the imaging means, and ensures to obtain a defect information on a stain of the assembled fiber band by using the scanning lines of the video signal obtained by scanning the region having a color similar to that of the assembled fiber band. The defect information on the thickness of the assembled fiber band may be detected by using the scanning lines of the video signal obtained by scanning the region of the similar color or low contrast color of the background plate, or by using the scanning lines of the video signal obtained by scanning the high contrast zones.

When a distinction signal from the distinction means becomes outside of reference values corresponding to an abnormal information, an announcing (alerting) means may announce the abnormal information or outlier information based on the distinction signal.

Furthermore, the auto distinction system may comprise a sync-separating means for separating synchronizing signals from the video signal from the imaging means, a clamping means for clamping the image signal in response to the signal from this sync-separating means, an extracting means for extracting a defect signal with respect to thickness, width, and/or stain of the assembled fiber band from the generated clamped image signal, and a distinction means for discriminating suitability of the assembled fiber band by comparing the extracted defect signal with the reference signal corresponding to the above-mentioned characteristics.

More specifically, the system may comprise an extracting means for extracting a thickness defect signal from the clamped image signal with respect to the thickness of the assembled fiber band, a thickness distinction means for discriminating suitability of the thickness by comparing the extracted defect signal with a reference value of the thickness of the assembled fiber band;

an extracting means for extracting a width signal from the clamped image signal with respect to the width of the assembled fiber band, a width distinction means for discriminating suitability of the width by comparing the extracted width signal with a reference value concerning the width of the assembled fiber band;

an extracting means for extracting a stain signal from the clamped image signal with respect to a stain of the assembled fiber band (for example, a differentiation means for differentiating the clamped image signal), and a stain distinction means for discriminating suitability or acceptability of the stain by comparing the extracted stain signal (for example, the differentiated clamped image signal) with a reference value concerning the stain of the assembled fiber band.

Furthermore, the system of the present invention may comprise a thickness distinction means which eliminates noise from the clamped image signal with respect to the thickness of the assembled fiber band and discriminates suitability of the thickness by comparing the noise-eliminated clamped image signal (or a fluctuation value of the image signal) with reference values concerning the thickness of the assembled fiber band (for example, an upper limit reference value and a lower limit reference value by means of a window comparator);

an extracting means which eliminates noise from the clamped image signal with respect to the width of the assembled fiber band and generates a rectangular signal corresponding to the width of the assembled fiber band, a counter means for counting rectangular sections of the clamped image signal on the basis of a clock means, a width distinction means for discriminating suitability of the width by comparing the count value obtained from the counter means with reference values concerning the width of the assembled fiber band;

a differentiation means for differentiating the clamped scanning signal with respect to the stain of the assembled fiber band, a comparing means for discriminating a large stain by comparing the differentiated clamped signal with reference values with respect to the stain of the assembled fiber band, a counter means for counting the number of stains on the basis of both the defect information on the stain from this comparing means and the information on the image width from the imaging means, and a stain distinction means for discriminating suitability or acceptability of the stain by comparing the count data counted by the counter means with a reference value regarding the stain of the assembled fiber band. In this system, the comparing means may comprise a first comparing means for discriminating a larger stain by comparing the differentiated clamped image signal and a first reference value with respect to stain largeness of the assembled fiber band, and a second comparing means for discriminating a smaller stain by comparing the differentiated clamped image signal and a second reference value with respect to stain smallness of the assembled fiber band. Furthermore, the counter means may comprise a first counter means for counting the number of large stains on the basis of both the defect information on the stain from the first comparing means and the information on the image width from the imaging means, and a second counter means for counting the number of small stains on the basis of both the defect information on stains from the second comparing means and the information on the image width from the imaging means. Furthermore, the stain distinction means may discriminate suitability or acceptability of the stain by comparing the count data counted by the first counter means and reference values with respect to large stains of the assembled fiber band.

Furthermore, the distinction system of the present method comprising imaging a continuously moving assembled fiber band by an imaging means, sync-separating and clamping a video signal from the imaging means, detecting a characteristic information containing a defect information with respect to at least one characteristic selected from a width, a thickness, and a stain of the assembled fiber band on the basis of a clamped image signal, extracting a defect information with respect to the characteristic from the detected characteristic information, and discriminating suitability of the defect information on the basis of the extracted signal and a reference signal with respect to the above-mentioned information (the detected characteristic information or defect information).

In this specification, "characteristic information" is sometimes just referred to as "information".

DETAILED DESCRIPTION OF THE PRESENT INVENTION

Figure 1:
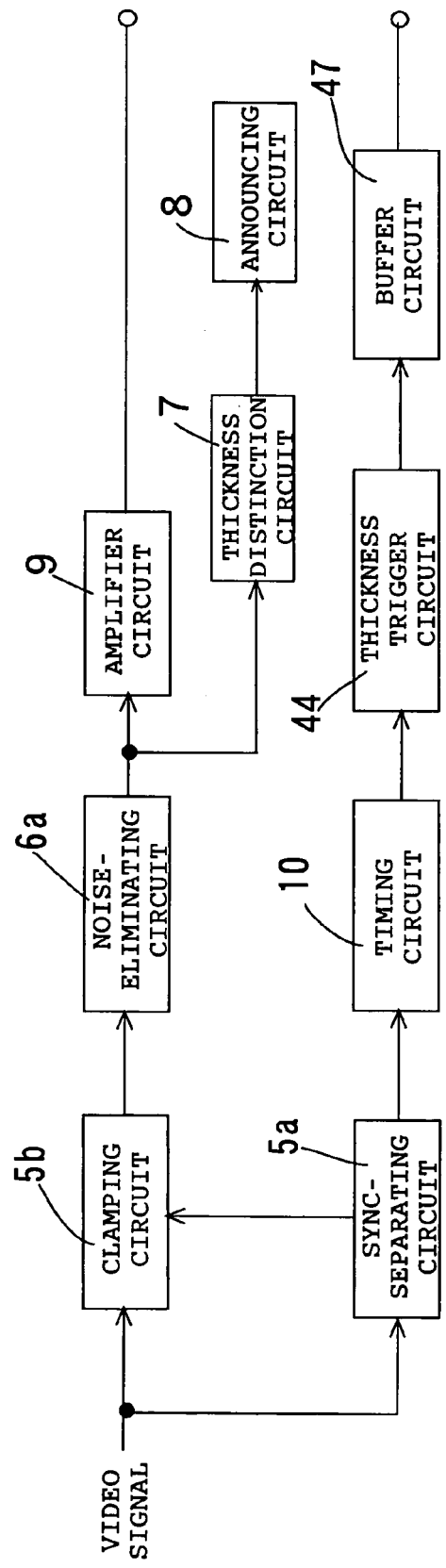
FIG. 1 is a block diagram showing an example of the electrical construction of the system of the present invention.
Figure 2:
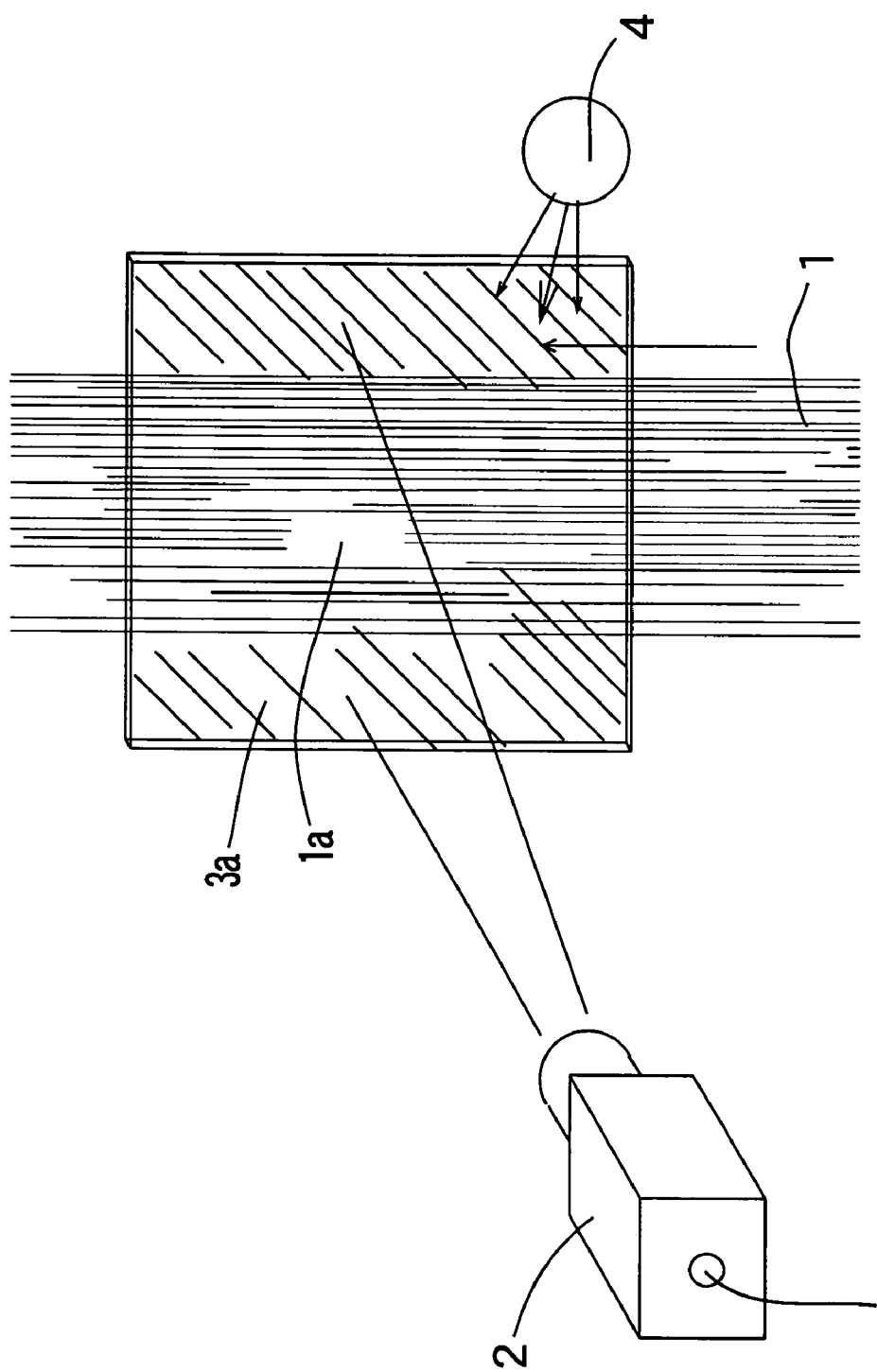
FIG. 2 is a schematic layout drawing of the system of FIG. 1.
Figure 3:
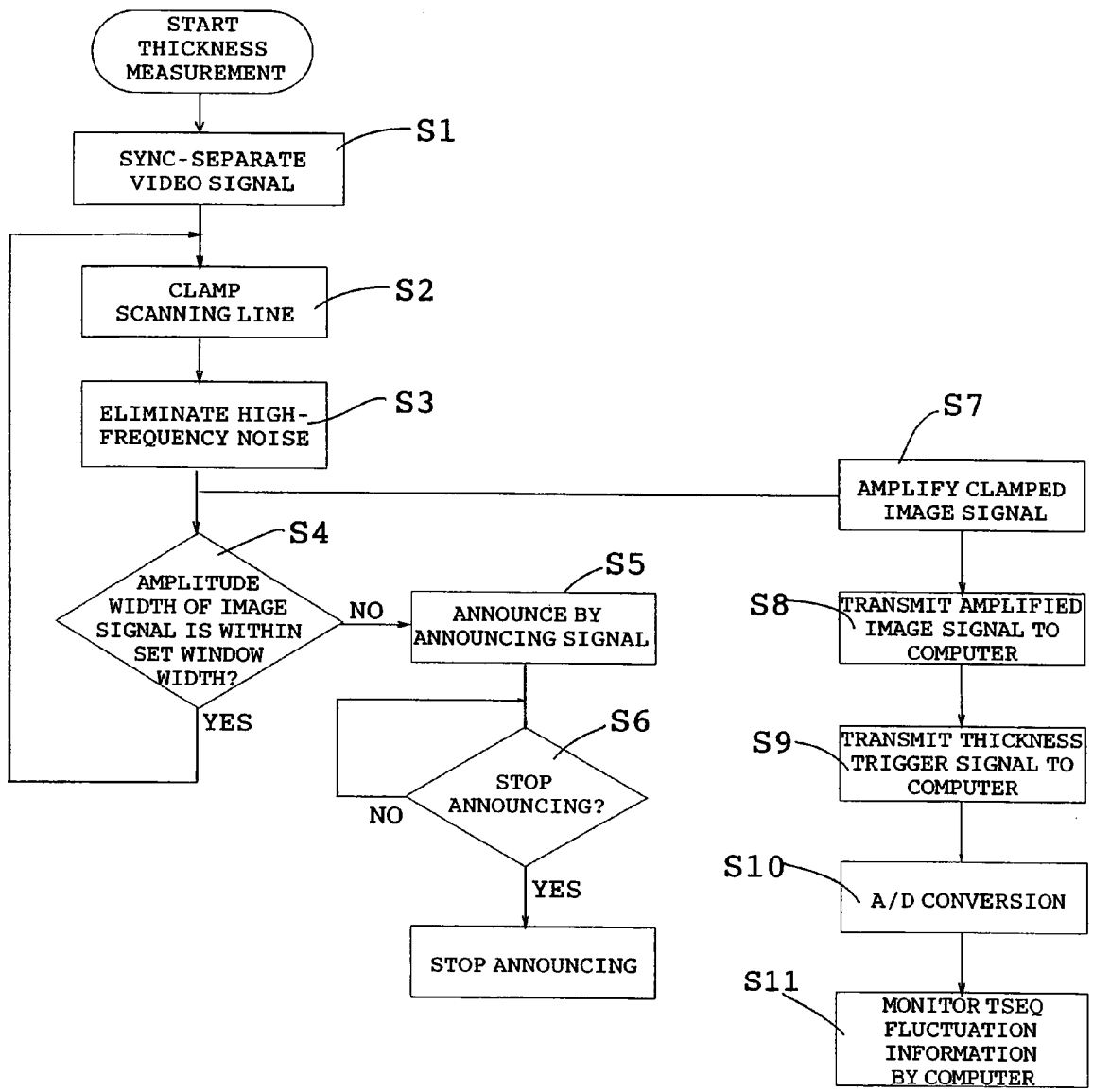
FIG. 3 is a flowchart for illustrating operations of the system of FIG. 1.

FIG. 1 is a block diagram showing an example of the electrical construction of the system of the present invention, FIG. 2 is a schematic layout drawing of the system of FIG. 1, and FIG. 3 is a flowchart for illustrating operations of the system of FIG. 1. In this example, thickness (or uneven thickness) of filter tow (band-shaped tow) which continuously moves are detected. The filter tow (or tow band) comprises a plurality of yarns. Namely, the filter tow is formed of a plurality of yarns which are bundled, adjacently arrayed each other, and overlapped into a layer form. Therefore, the degrees of adjacency and overlapping of the yarns adjacent to each other fluctuate as yarns move, and unevenness in thickness of the filter tow easily generates a defective product.

As shown in FIG. 2, on the foreside of a filter tow 1 which continuously moves from the lower side to the upper side, a video camera (imaging means) 2 is provided with a predetermined angle of view, and on the backside of the filter tow 1, a black background plate 3a is provided for increasing the contrast to the white tow. In an out-of-view field range of the video camera 2, an illumination unit 4 for illuminating the filter tow 1 from an oblique direction is provided on the backside of the filter tow 1. Namely, the illumination unit 4 is disposed so as to face the backside of the filter tow 1 from the background plate 3a, and illuminates (or permeably illuminates) the backside of the filter tow 1 with light beams. Therefore, by means of the difference of light transmittances in filter tow 1, namely high light transmittance in a thin region 1a and low light transmittance in a thick region, the thickness (or thinness) of the filter tow 1 can be imaged with high contrast and the evenness or unevenness in thickness thereof can be detected with high accuracy.

A video signal from an image sensor (CCD, imaging tube or image pick up tube, etc.) of the video camera contains, in interlace scanning, signals of a horizontal blanking section (or period) and an image section forming one scanning line, a signal forming a vertical blanking section (or period) (vertical synchronizing signal (vertical sync pulse), serrated pulse, equalizing pulse, etc.). A signal forming the horizontal blanking section (or period) contains a front-porch region, a horizontal synchronizing signal, and a back-porch region, etc.

Such a video signal (in particular, at least a luminance signal out of the video signal) is supplied to a sync-separating circuit 5a, and this sync-separating circuit separates various synchronizing signals (the horizontal synchronizing signal, the vertical synchronizing signal, a frame synchronizing signal, odd-number and even-number signals respectively corresponding to odd-number fields and even-number fields, and sync-clamping signals, etc.) from the video signal to generate the above-mentioned various synchronizing signals. The sync-clamping signals separated and generated from the video signal by the sync-separating circuit 5a are supplied to a clamping circuit 5b. This clamping circuit clamps the video signal in response to the sync-clamping signal, and makes the reference level constant. More specifically, since an AC-coupled video signal changes its amplitude depending on the size of the image signal section, the DC levels of the synchronizing signals are not constant, nor are the DC levels of the video signal superimposed on the synchronizing signals not constant. Therefore, a sync-clamping signal is generated by the sync-separating circuit 5a for separating synchronizing signals from the video signal, and by this signal, the video signal is clamped, the DC levels are regenerated and the reference level is made constant.

The image signal (in particular, at least a luminance signal) from the video signal contains various information (characteristic information including defect information) with respect to the filter tow. Therefore, in order to extract the defect information with respect to the thickness from a predetermined scanning line (for example, an X-th scanning line across the imaging region or field) of the video signal, a clamped image signal (scanning signal) of the predetermined scanning line is supplied to an extraction circuit (or detection circuit). In this example, since the characteristic information with respect to the thickness of the tow is usually contained in a clamped image signal as a low frequency signal, the extraction circuit (or detection circuit) comprises a high-frequency noise-eliminating circuit (low-pass filter circuit) 6a. That is, the image signal that has been clamped (clamped image signal) contains noise within the suitable or acceptable thickness range due to fine unevenness of fibers (or filaments) or yarns. Therefore, the clamped image signal is supplied to the noise-eliminating circuit (low-pass filter circuit) 6a for noise elimination, and the clamped image signal from which noise has been eliminated is supplied to a thickness distinction circuit 7 for comparison with reference values (each of thresholds of the lower limit and the upper limit of the thickness) with respect to the thickness of the filter tow. This thickness distinction circuit 7 comprises a window comparator, and generates an announcing signal when the signal level of the image signal (fluctuation value) becomes outside of a set (predetermined) window width. Namely, in the thickness distinction circuit (window comparator) 7, the lower limit reference value (lower limit threshold) and the upper limit reference value (upper limit threshold) regarding the thickness are compared with the clamped image signal (fluctuation value). When the clamped image signal level is equal to or lower than the lower limit threshold, or equal to or higher than the upper limit threshold, the distinction circuit 7 discriminates that the tow is defective. When the clamped image signal level is equal to or lower than the lower limit threshold, or equal to or higher than the upper limit threshold, the thickness distinction circuit 7 supplies an announcing signal to an announcing circuit 8 to announce that an abnormality or defect occurs in the thickness of the filter tow.

Incidentally, the clamped image signal from which noise has been eliminated is amplified by an amplifier circuit 9 which forms an interface to the outside, and the amplified image signal is supplied to the process controlling computer (process control unit). That is, in response to various signals from the sync-separating circuit 5a, a timing circuit 10 generates various timing signals from the video signal, and supplies the timing signals to a thickness trigger circuit 44. The thickness trigger circuit 44 is used for transmitting or transferring (data taking-in) the characteristic information (the amplified clamped image signal) to the computer via a buffer circuit 47 which forms an interface to the outside in order to supply a trigger signal to the computer. Incidentally, the image signal (characteristic information signal) is analog-digital (A/D) converted and taken-in as a digital signal in the computer. Therefore, the time sequence fluctuation information (time-series fluctuation information) with respect to the thickness of the filter tow can be controlled by a computer, and can be utilized for process control and quality control in the manufacturing process of the filter tow. For example, on the basis of the level or scale of the defect information, statistical data processing (time sequence fluctuation trend, generation frequency of the defect information (including the level and scale) and so on), the information can be utilized for control of the manufacturing process of the filter tow.

In the above-mentioned system, as shown in FIG. 3, when thickness measurement is started, a video signal is subjected to sync-separating in Step S1. The video image signal is clamped by a sync-clamping signal generated by sync-separating in Step S2, and high frequency noise is eliminated from the clamped image signal and the defect information with respect to the thickness is extracted in Step S3. The clamped image signal from which noise has been eliminated is discriminated in Step S4 whether or not the amplitude width (width information) of the image signal is within or without a set window width (reference value range), and when the amplitude width is within the window width range, the process returns to the above-mentioned Step S2 and continues the same operation. On the other hand, when the image amplitude width becomes outside of the set window width, it is informed by an announcing signal announces (alerts) that a thickness abnormality or defect has occurred in Step S5, and in Step S6, it is determined whether or not warning (announcing) is to be stopped, and unless the warning (announcing) is stopped, the warning (announcing) is continued, and announcing is ended by stopping the warning (announcing).

The clamped image signal from which noise has been eliminated is amplified in Step S7. In Step S8, the amplified clamped image signal is transmitted to the computer, and in Step S9, a thickness trigger signal is supplied to the computer. In Step S10 for taking-in the clamped image signal into the computer, an analog signal is converted into a digital signal (A/D conversion), and in Step S11, the digitized clamped image signal is used as a time sequence (TSEQ) fluctuation information by the computer.

Figure 4:
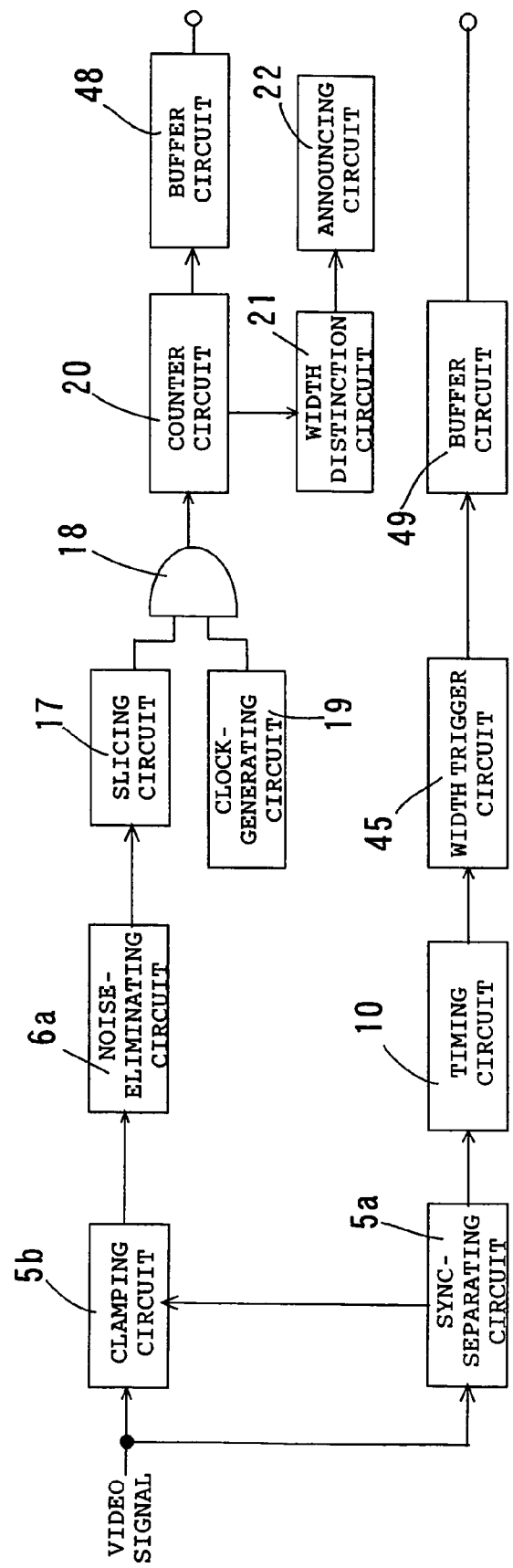
FIG. 4 is a block diagram showing another example of the electrical construction of the system of the present invention.
Figure 5:
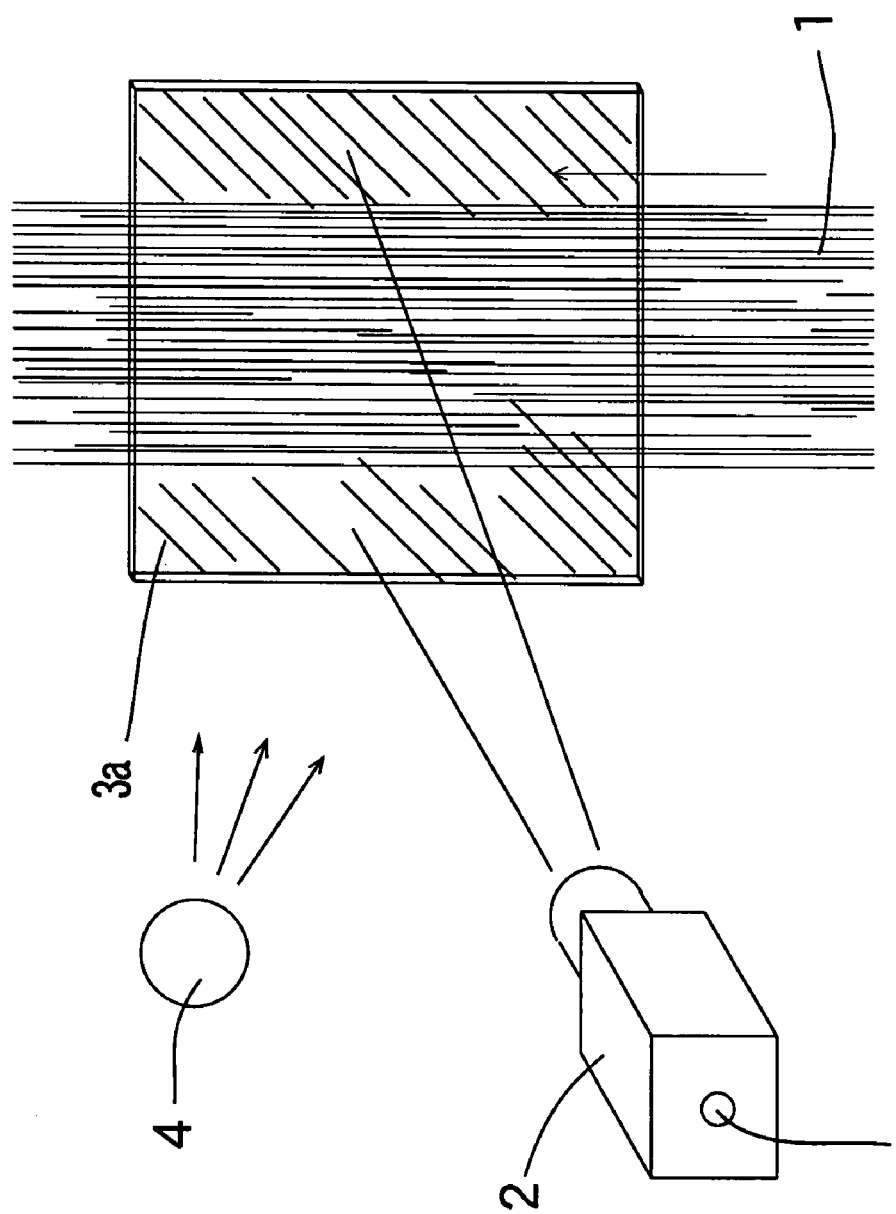
FIG. 5 is a schematic layout drawing of the system of FIG. 4.
Figure 6:
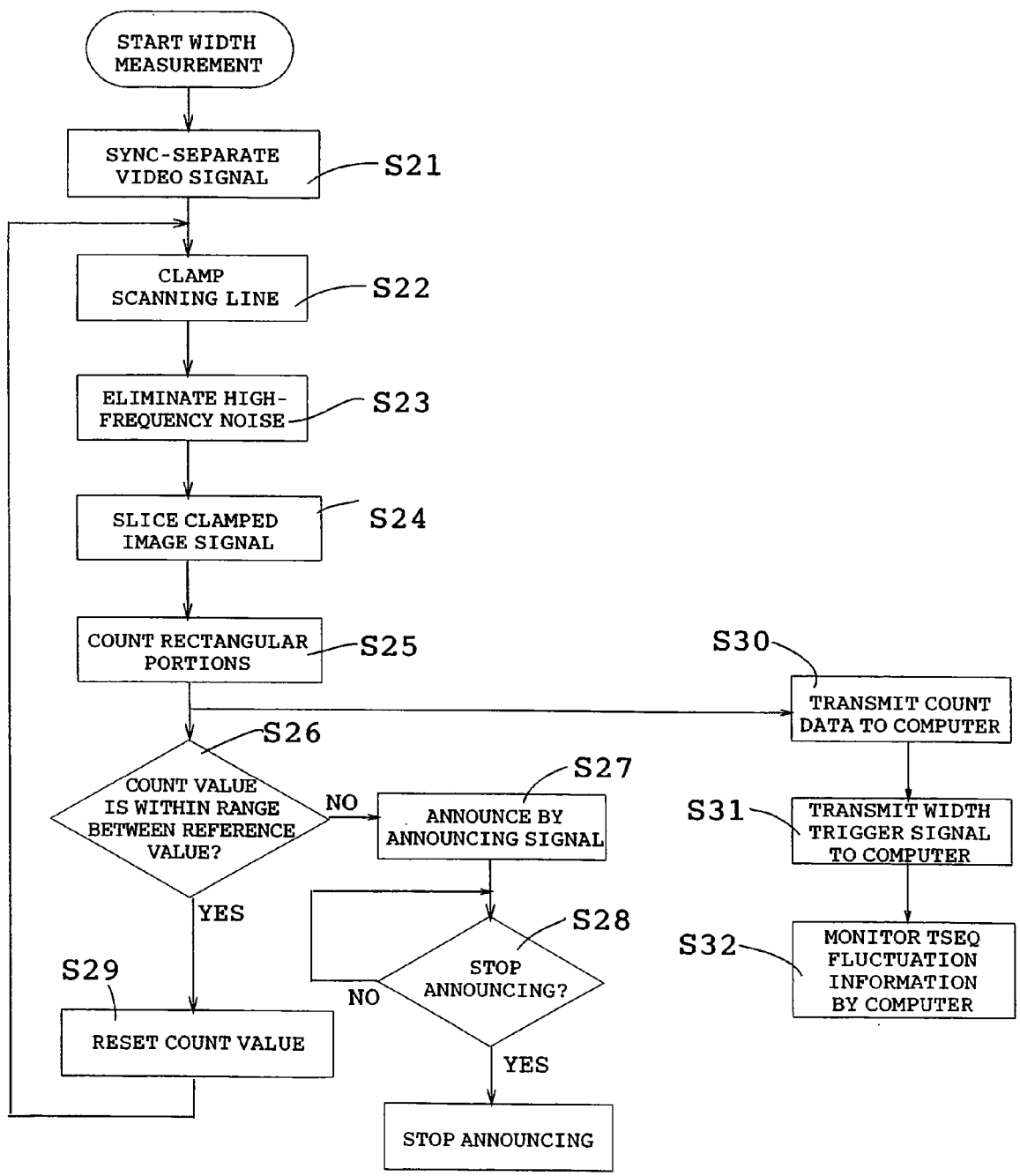
FIG. 6 is a flowchart for illustrating operations of the system of FIG. 4.

FIG. 4 is a block diagram showing another example of the electrical construction of the system of the present invention, FIG. 5 is a schematic layout drawing of the system of FIG. 4, and FIG. 6 is a flowchart for illustrating operations of the system of FIG. 4. In this example, width of a filter tow (band-shaped or ribbon-shaped tow) which continuously moves is detected.

As shown in FIG. 5, in this example, a background plate 3a and a video camera 2 are disposed with respect to the filter tow 1 in the same manner as in FIG. 2 except that the illumination unit 4 is disposed on the side of the video camera 2 (that is, the front side of the filter tow 1).

The video signal from the video camera 2 (in particular, at least a luminance signal in the video signal) is supplied to a sync-separating circuit 5a in the same manner as described above, and in response to a sync-clamping signal from this sync-separating circuit 5a, a clamping circuit 5b clamps the video signal to make the reference level constant. The synchronizing signals separated from the video signal are supplied to a timing circuit 10, and this timing circuit generates various timing signals in order to synchronize with an image signal corresponding to a predetermined scanning line.

The characteristic information with respect to the width of the tow is included in the clamped image signal as a low frequency signal. Therefore, in order to eliminate noise from the video signal and the extract information with respect to the width of the tow, the video signal of a predetermined scanning line containing the characteristic information with respect to the width of the tow (the clamped image signal, in particular, at least the luminance signal) is supplied to an extraction circuit comprising a noise-eliminating circuit (or low-pass filter circuit) 6a for eliminating high frequency noise, and a slicing circuit 17. The noise-eliminating circuit 6a eliminates noise contained in the clamped image signal (that is, noise signals which are outside of the image signal, noise signals at the rising and lowering points of the image signal, and noise signals which are inside of the image signal), and generates an image signal from which noise has been eliminated. Furthermore, in order to extract a signal with respect to the width of the tow with higher accuracy, the image signal is supplied to a slicing circuit (or comparing circuit) 17 with predetermined thresholds set, and this slicing circuit 17 generates a rectangular signal sliced at a predetermined level corresponding to the width of the tow.

The noise-eliminated and sliced rectangular signal is supplied to an AND circuit 18, and a reference clock signal (pulse signal) from a clock-generating circuit 19 is also supplied to this AND circuit. Therefore, the AND circuit 18 generates a clock signal (pulse signal) corresponding to the sliced rectangular wave field. The signal from the AND circuit 18 is supplied to a counter circuit 20, and the clock number (pulse number) corresponding to the width of the sliced rectangular wave is counted. For resetting the count data counted by the counter circuit 20 for each scanning of one image plane, that is, for each field scanning, the timing circuit 10 supplies a timing signal to a resetting circuit (not shown), and this resetting circuit resets the accumulated count data counted by the counter circuit 20 in response to the timing signal supplied from the timing circuit 10.

The count signal from the counter circuit 20 is supplied to a width distinction circuit 21 for discriminating suitability of the width of the filter tow by comparing the count signal with reference values with respect to the width of the filter tow. Incidentally, as reference values with respect to the width of the filter tow, a lower limit reference value (lower limit threshold) and an upper limit reference value (upper limit threshold) can be used, and when the counter signal (count data) is equal to or lower than the lower limit threshold or equal to or higher than the upper limit threshold, the width can be determined as defective and suitability of the width is discriminated. When the width of the filter tow is determined as defective, the width distinction circuit 21 supplies an announcing signal to an announcing circuit 22 to announce that an abnormality or defect with respect to the width of the filter tow has occurred.

Incidentally, the signal from the counter circuit 20 is supplied to the computer (an external computer such as a process controlling computer) via a buffer circuit 48 which forms an interface to the outside. To this computer, a trigger signal for taking-in data is supplied. Namely, in response to various signals from the sync-separating circuit 5a, the timing circuit 10 generates various timing signals with respect to scanning lines of the video signal. The timing signals from the timing circuit 10 are supplied to a width trigger circuit 45, and the width trigger circuit supplies a trigger signal to the computer via a buffer circuit 49 forming an interface to the outside, and this trigger signal is used for transmission or transfer (data taking-in) of the characteristic information (count data) to the computer via the interface. That is, the time sequence fluctuation information (time-series fluctuation information) with respect to the width of the filter tow can be controlled by the computer, and can be used for process control and quality control in the manufacturing process of the filter tow. For example, based on fluctuation band with respect to the width, and statistical data processing (e.g., time-series fluctuation trend of width and generation frequency of the defect information), the information can be used for process control in the filter tow production.

In this system, as shown in FIG. 6, when width measurement is started, in Step S21 a video signal is subjected to sync-separating, and a video image signal is clamped by a sync-clamping signal generated from sync-separating, in Step S22. In Step S23 high frequency noise is eliminated from the clamped image signal, and in Step S24 the image signal is sliced to extract the characteristic information on the width. The characteristic information (width of the sliced rectangular signal or rectangular wave) extracted in Step 24 is counted on the basis of a reference clock signal in Step S25, and it is discriminated in Step S26 whether or not the count data is within or without the range between reference values (upper limit and lower limit values). When the count data becomes outside of the range between reference values, in Step S27 it is informed with an announcing signal that an abnormality or defect in the width has occurred, and in Step S28 it is discriminated or judged whether or not the announcing is to be stopped. When the announcing is not stopped, the announcing is continued, and when the announcing is to be stopped, the announcing is ended. On the other hand, when the count data is within the range between the reference values, the count data is reset to zero in Step S29 and the process returns to the above-mentioned Step S22.

Furthermore, in Step S30, the count data counted in the above-mentioned Step S25 is transmitted or transferred to the computer, and in Step S31, a width trigger signal is supplied to the computer. In response to this trigger signal, in Step S32, the computer monitors or analyzes the time sequence width fluctuation information (fluctuation information) based on the transmitted or transferred count data, and uses the count data for process control.

Figure 7:
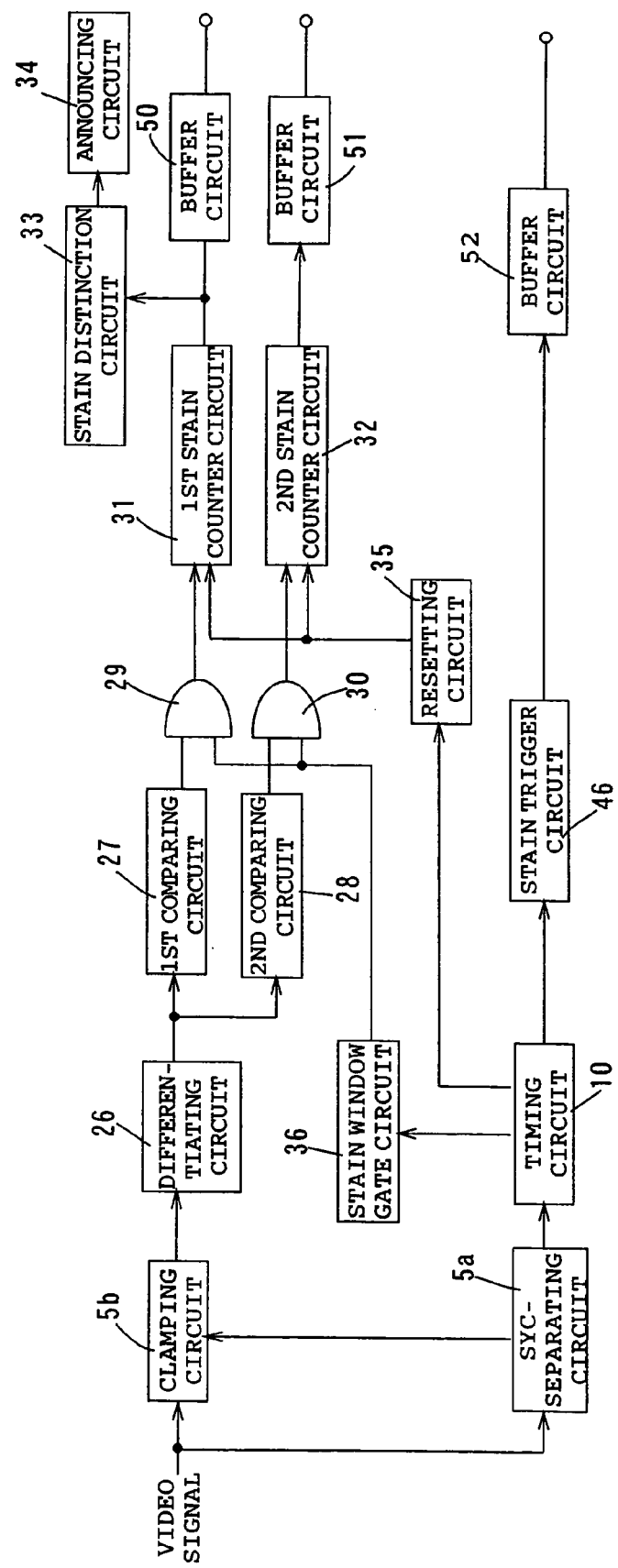
FIG. 7 is a block diagram showing still another example of the electrical construction of the system of the present invention.
Figure 8:
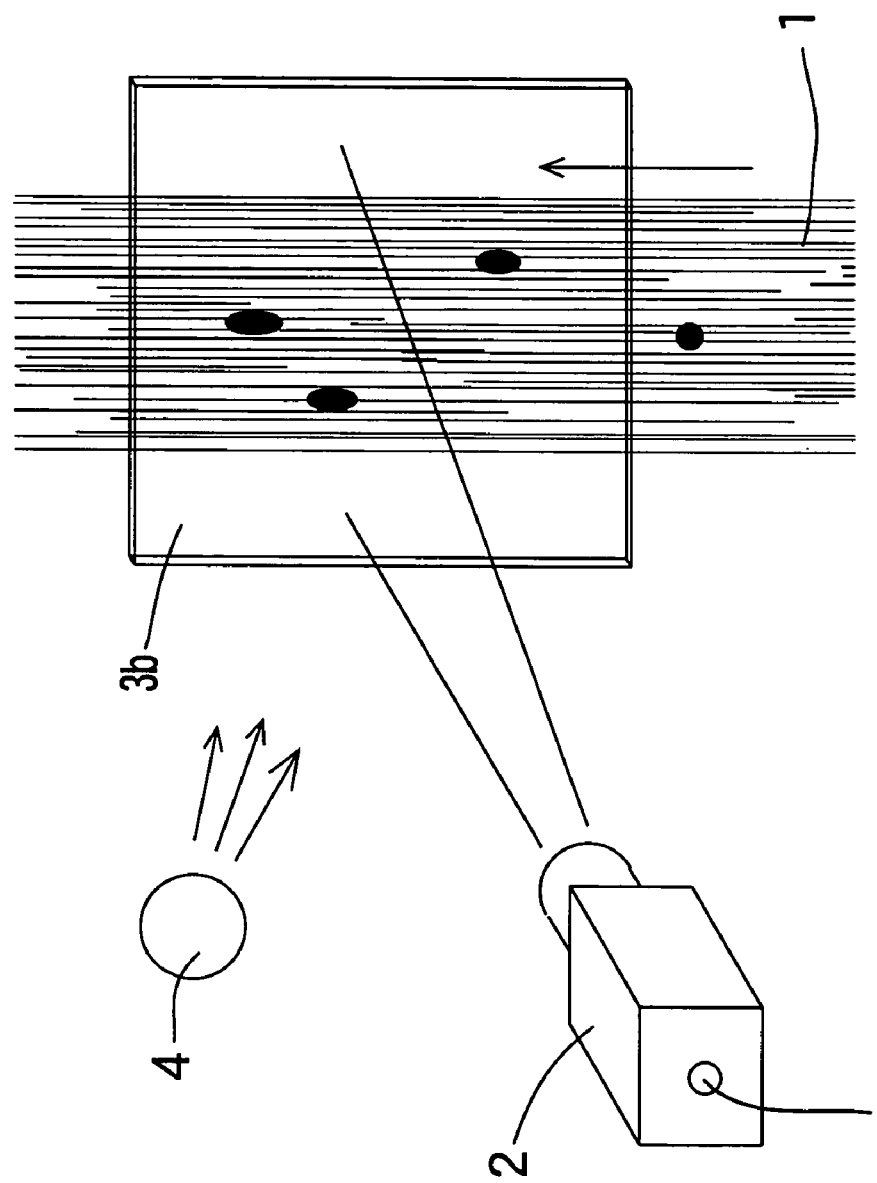
FIG. 8 is a schematic layout drawing of the system of FIG. 7.
Figure 9:
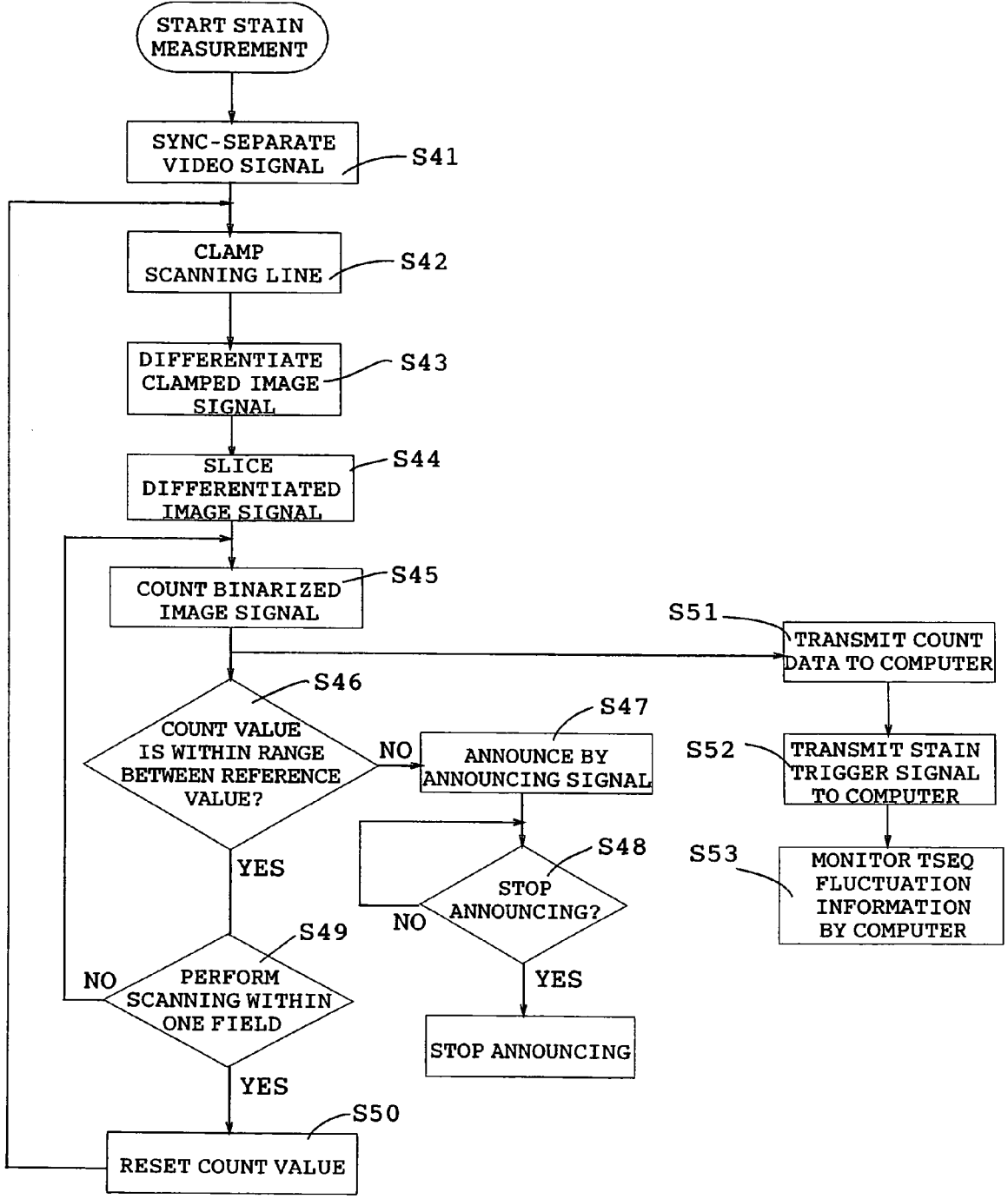
FIG. 9 is a flowchart for illustrating operations of the system of FIG. 7.

FIG. 7 is a block diagram showing still another example of the electrical construction of the system of the present invention, FIG. 8 is a schematic layout drawing of the system of FIG. 7, and FIG. 9 is a flowchart for illustrating operations of the system of FIG. 7. In this example, a stain on a filter tow (band-shaped tow) which continuously moves is detected.

As shown in FIG. 8, in this example, in order to efficiently extract a stain on the white filter tow 1 with preventing the stain extraction efficiency from lowering due to shadow, a video camera 2 and an illumination unit 4 are provided in the substantially same way with FIG. 5 except that a background plate 3b having a color similar to (color similar in brightness or white) the color of the filter tow 1 is used.

The video signal (in particular, at least a luminance signal) from the video camera 2 is, as in the description given above, supplied to a sync-separating circuit 5a, and in response to a sync-clamping signal from this sync-separating circuit, a clamping circuit 5b clamps the video signal to make the reference level constant. Synchronizing signals separated from the video signal are supplied to a timing circuit 10 from the sync-separating circuit 5a, and the timing circuit generates various timing signals for synchronization with an image signal with respect to a scanning line.

Stains of the tow are usually contained in the clamped image signal as a high frequency signal. Therefore, the clamped video signal (in particular, at least a luminance signal) is supplied to a differentiating circuit 26 comprising a low-pass filter for elimination of low frequency noise. In order to extract the defect information with respect to stains on the tow, the clamped image signal is supplied to an extraction circuit which comprises a differentiating circuit 26, a comparing circuit 27, and an AND circuit 29. Namely, in the differentiating circuit 26, the clamped image signal is differentiated to eliminate low frequency noise, and the defect information on the stain and others is also converted into a peak waveform. The differentiated signal generated from the differentiating circuit 26 is supplied to a high level stain comparing circuit (first comparing circuit) 27 for slicing or comparison at a slice level (or a threshold, first reference value) with respect to a high level stain, and a low level stain comparing circuit (second comparing circuit) 28 for slicing or comparison at a slice level (or a threshold, second reference value) with respect to a low level stain, and binarized signals are generated for stain detection. Incidentally the high level stain can be made to correspond to a value of a differentiated signal corresponding to an original stain of the filter tow, and the low level stain can be made to correspond to a value of a differentiated signal corresponding to a latent stain of the filter tow.

The differentiated signal and the binarized signals from the differentiating circuit 26 sometimes contains binarized noise signals corresponding to shadows in both-side regions of the moving filter tow. Therefore, by generating a gate signal slightly narrower than the width of the moving filter tow, and by supplying this gate signal and the binarized signals to the AND circuits, noise signals can be eliminated. In order to eliminate the noise signals, the signal from the first comparing circuit 27 and a tow width window gate signal from a stain window gate circuit 36 as the information with respect to the image width are supplied to a first AND circuit 29, and the signal from the second comparing circuit 28 and the tow width window invention may comprise a transmitting means for supplying the characteristic information [for example, at least one of characteristic information selected from a width count data (count data with respect to the width), a thickness clamped image signal (clamped image signal with respect to the thickness), and a stain count data (count data with respect to the stain)] to a process controlling computer (or an external computer through the interface means). As the stain count data, data on the above-mentioned stains (large stain count data and/or small stain count data) can be used. This transmitting means may comprise an interface means for transmitting or transferring the characteristic information (at least one of characteristic information selected from a width count data, a thickness clamped image signal, and a stain count data) to the computer, and a trigger means for generating a trigger signal announcing transferring timing of the characteristic information to the process controlling computer (or external computer). When such a transmitting or transferring means is provided, a characteristic information including a defect information with respect to at least one characteristic selected from a thickness, a width, and a stain of the assembled fiber band can be used as a time sequence fluctuation information (time-series fluctuation information) and can be used for process control or quality control by a process control unit.

The present invention also includes auto distinction gate signal from the stain window gate circuit 36 are supplied to a second AND circuit 30. Then noise is eliminated which corresponds to shadows on both-side portions caused by the background plate and is selected from the differentiated signal and the binarized signals from the differentiating circuit 26. Incidentally in the stain window gate circuit 36, a window slightly narrower than the set window width (observation width) of the filter tow, namely, a width reference value with respect to window width which does not contain the noise, is set, and the window gate signal from the stain window gate circuit 36 is supplied to the AND circuits 29 and 30 at a predetermined timing from the timing circuit 10 which generates synchronizing signals (timing signals) with respect to scanning lines of the video signal.

Binarized signals from the first and second AND circuits 29 and 30 are supplied to stain counter circuits 31 and 32, respectively, and the number of pulses or rectangular peaks corresponding to stains in the binarized signals is counted. Incidentally, a count signal from the second counter circuit 32 is used for control of latent stains of the filter tow.

A count signal (signal with respect to the count data) from the first counter circuit 31 is supplied to a stain distinction circuit 33 for discriminating suitability or acceptability of the stain by comparison with predetermined reference values with respect to stains on the assembled fiber band, and when the degree of the stain (count number) becomes equal to or larger than a predetermined reference value, the stain distinction circuit 33 supplies an announcing signal to an announcing circuit 34 to announce that the stain on the filter tow is large.

For resetting count data of the first stain counter circuit 31 and the second stain counter circuit 32 for each scanning one image plane, that is, for each field scanning, the timing circuit 10 supplies a timing signal to a resetting circuit 35, and the resetting circuit responds to the timing signal from the timing circuit so that the count data accumulated in the first and second counter circuits 31 and 32 is reset to zero.

Furthermore, the count signals from the first counter circuit 31 and the second counter circuit 32 are supplied to the computer via buffer circuits 50 and 51, respectively, and the buffer circuits form interfaces to the outside. Accordingly, the count signals are used for displaying the degree of the stain on a display or for process control of the filter tow. Namely, in response to various signals from the sync-separating circuit 5a, the timing circuit 10 generates various timing signals with respect to scanning lines of the video signal, and supplies the timing signals to a stain trigger circuit 46. This stain trigger circuit supplies, in response to the timing signals, a trigger signal to the computer via a buffer circuit 52 which forms an interface to the outside, and this trigger signal is used for transmission or transfer (data taking-in) of the characteristic information (stain count data or count signals) to the computer via the interface.

In the distinction system, as shown in FIG. 9, the video signal is subjected to sync-separating in Step S41 in response to a starting signal regarding stain measurement, and the video image signal is clamped by the sync-clamping signal generated by means of sync-separating in Step S42. The clamped image signal is differentiated in Step S43 for elimination of noise, and sliced and binarized in Step S44. In Step S45, the binarized image signals (pulses or rectangular peaks) are counted. It is discriminated whether or not the count signal (a signal with respect to the count data or count data) is within or without the range of reference values in Step S46, and when the count data becomes outside of the reference value range, generation of a stain abnormality or defect is announced in Step S47 by means of an announcing signal. In Step S48 it is discriminated whether or not the announcing (warning) is stopped, and if announcing is not stopped, announcing is continued, and if announcing (warning) is stopped, announcing is stopped or ended. On the other hand, when the count data is within the range of reference values, it is discriminated whether or not scanning was performed within or without one field in Step S49, and when scanning is not performed within one field the process returns to Step S45 for counting the binarized signals, and after scanning is performed within one field, the count data is reset to zero in Step S50.

Furthermore, in Step S51, the count data counted in Step S45 is transmitted or transferred to the computer, and in Step S52, a stain trigger signal is supplied to the computer. In Step S53, in response to this trigger signal, the computer monitors or analyzes the time sequence stain fluctuation information (time sequence fluctuation information) based on the transmitted or transferred count data, and uses the count data for process control.

Incidentally, in this flowchart, for the sake of convenience, slicings with respect to the high level stain and the low level stain are referred to as slicing in one Step S44, and counting of high level stains and counting of low level stains are referred to as counting of binarized signals in one Step S45. Therefore, processing after Step S46 is carried out for both the high level stain counting and the low level stain counting.

Incidentally, in the above-mentioned example, a defect information (thickness, width, or stain) of the moving filter tow is detected and it is discriminated whether the filter tow is non-defective or defective. However, in the present invention also ensures to discriminate whether the filter tow is non-defective or defective by detecting the defect information with respect to at least two characteristics or all characteristics of the thickness, width, and stain of the filter tow.

Figure 10:
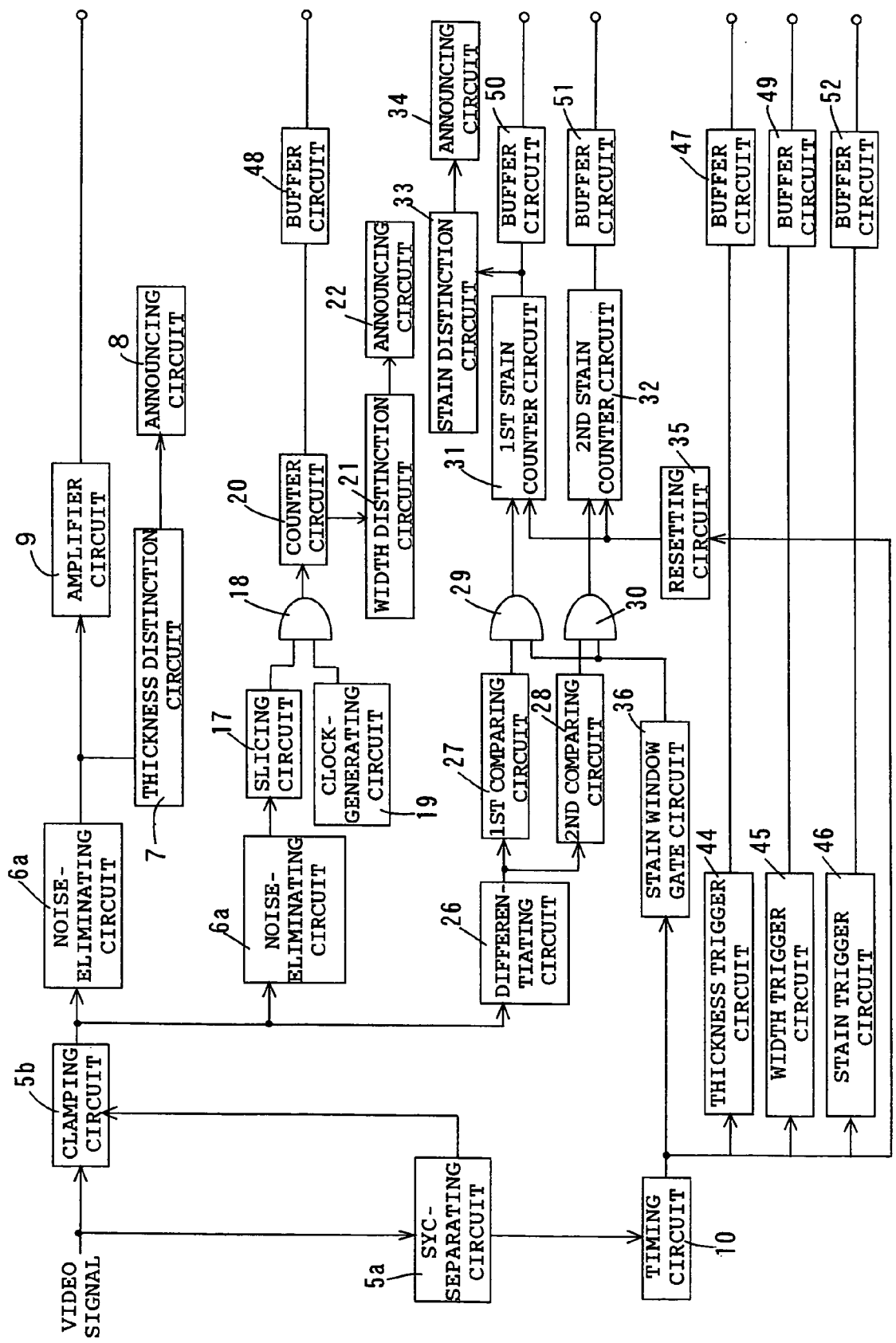
FIG. 10 is a block diagram showing another example of the electrical construction of the system of the present invention.
Figure 11:
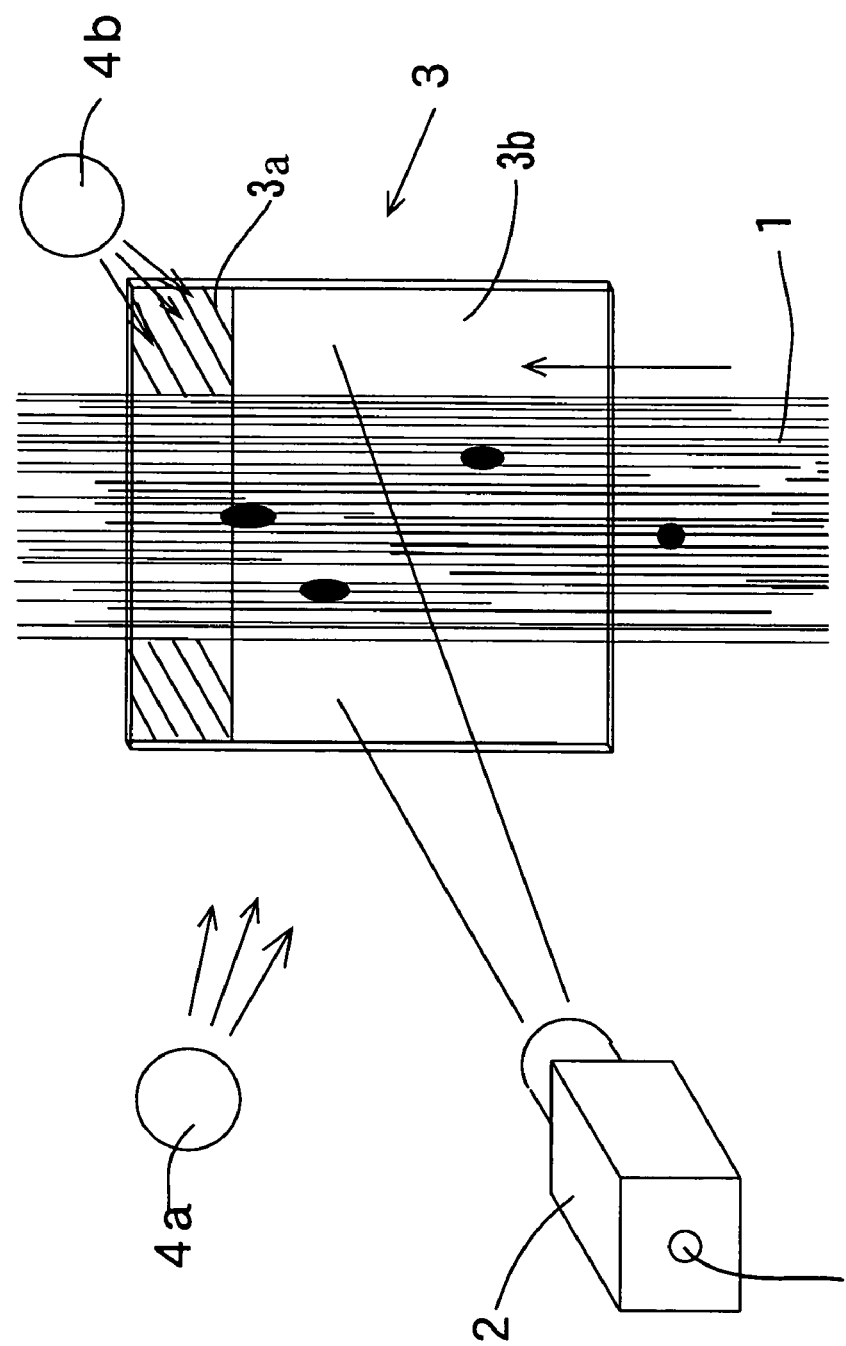
FIG. 11 is a schematic layout drawing of the system of FIG. 10.
Figure 12:
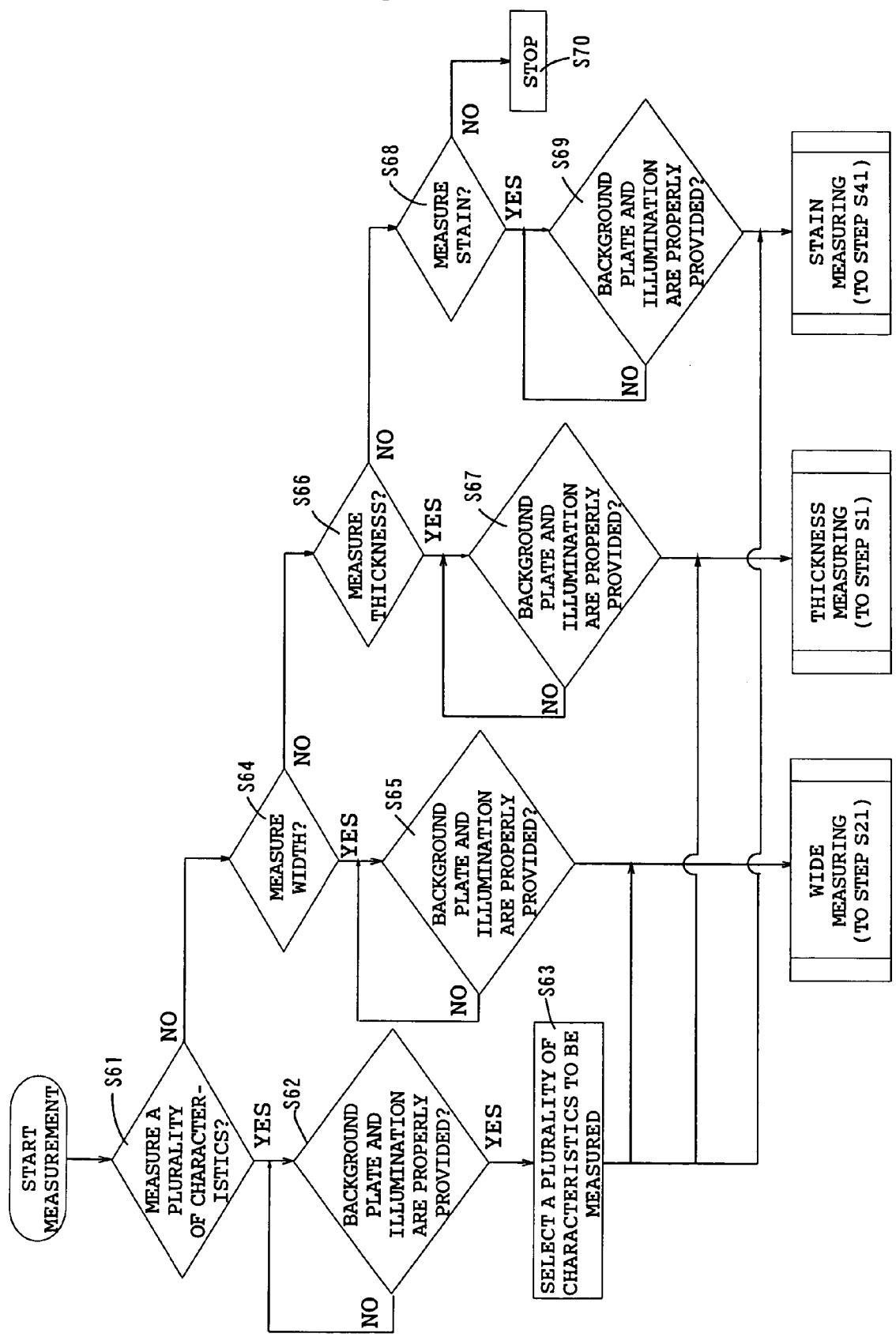
FIG. 12 is a flowchart for illustrating operations of the system of FIG. 10.

FIG. 10 is a block diagram showing another example of the electrical construction of the system of the present invention, FIG. 11 is a schematic layout drawing of the system of FIG. 10, and FIG. 12 is a flowchart for illustrating operations of the system of FIG. 10. In this example, the thickness, width, and stain of a filter tow (band-shaped tow) which continuously moves are detected.

As shown in FIG. 11, in this example, a background plate 3 disposed on the backside of the filter tow 1 has a white region 3b and black zones 3a. The white region 3b has a color (white) similar to the color of the filter tow 1 in order to increase the stain detection accuracy, and the black zones 3a which are formed with a predetermined width on the upper portion and lower portion of the background plate 3 and have high contrast to the filter tow 1 for detecting the width of the filter tow accurately. Incidentally, a video camera 2 and an illumination unit 4a are disposed in the same positional relationship as in the above-mentioned FIG. 5, and an illumination unit 4b is disposed in the same positional relationship as in the above-mentioned FIG. 2.

As shown in FIG. 12, in this system, in response to measurement start signal, mode selection is required for selecting the characteristics of the filter tow to be measured. That is, in Step S61 it is required to select whether or not a plurality of characteristics of the filter tow are to be measured, and when it is selected that a plurality of characteristics are to be measured, in Step S62, a distinction is required as to whether or not the background plate and the illuminations (or illumination units) have been properly disposed (for example, whether or not a two-colored background plate has been set and the front illumination and back illumination have been provided). When the background plate and the illumination units are not properly provided, it is required to set the background plate and the illumination units properly. When the background plate and illuminations are properly set, it is required in Step S63 to select a plurality of characteristics to be measured. When a plurality of characteristics are selected from a thickness, a width, and a stain of the filter tow, the process transfers to Step S1 shown in the above-mentioned FIG. 3, Step S21 shown in FIG. 6, and Step S41 shown in FIG. 9, and measurement of each characteristic is started.

On the other hand, when measurement of a plurality of characteristics is not selected in the above-mentioned Step S61, it is required to select whether or not the width of the filter tow is to be measured in Step S64, and in Step S64, when the width measurement is selected, it is required to discriminate whether or not the background plate and illumination have been properly set (for example, whether or not the black background plate has been set and the front illumination has been provided), and when the background plate and the illuminations are not properly set, it is required to properly set the background plate and the illuminations. When the background plate and the illumination are properly set, the process transfers to Step S21 shown in the above-mentioned FIG. 6. On the other hand, when the width measurement is not selected in Step S64, it is required in Step S66 to select whether or not the thickness measurement of the filter tow is to be selected. When the width measurement is selected in Step S66, it is required to discriminate whether or not the background plate and illumination have been properly set (for example, whether or not the black background plate has been set and the back illumination has been provided). When the background plate and the illuminations are not properly set, it is required to set properly the background plate and the illuminations. When the background plate and the illuminations are properly set, the process transfers to Step S1 shown in the above-mentioned FIG. 3. Furthermore, when the thickness measurement is not selected in the above-mentioned Step S66, it is required in Step S68 to select whether or not the stain of the filter tow is to be measured. When the stain measurement of the filter tow is selected in Step S68, it is required in Step S69 to discriminate whether or not the background plate and the illuminations have been properly set (for example, whether or not a white back plate has been set and the front illumination has been provided). When the background plate and the illuminations are not properly set, it is required to set the background plate and the illuminations properly. When the background plate and the illuminations are properly set, the process transfers to Step S41 shown in the above-mentioned FIG. 9. Furthermore, when the stain measurement is not selected in Step S68, the measurement operation is stopped in Step S70. Incidentally, considering a case of erroneous inputs, it is possible to return to Step S61 again without stopping measurement in Step S70, or it is possible to provide a proper step for canceling the data which has been already input.

Incidentally, when a plurality of characteristics are not measured, the measurement order of the thickness, width, and stain of the filter tow is not particularly limited to a specific one, and the measurement order of the characteristics may be arbitrary. Incidentally, it is preferred that, as a select mode, the width measurement mode is made to precede the thickness or stain measurement modes for the sake of disposition of the background plate and illuminations.

As shown in FIG. 10, a video signal (in particular, at least a luminance signal) from the video camera 2 is supplied to the sync-separating circuit 5a as described above, and in response to a sync-clamping signal from this sync-separating circuit, the clamping circuit 5b clamps the video signal, regenerates the DC level of the image signal, and makes the reference level constant. Synchronizing signals (timing signals) with respect to scanning lines separated from the video signal by the sync-separating circuit 5a are supplied to the timing circuit 10, and this timing circuit generates various timing signals for synchronization with the image signal.

A signal (clamped image signal) of a predetermined scanning line (for example, a Z-th scanning line across the black zone), which is generated from the clamping circuit 5b and is obtained from scanning the black zone 3a of the background plate 3, is supplied to the noise-eliminating circuit (low-pass filter circuit) 6a which forms an extraction circuit, and a clamped image signal from which noise has been eliminated is supplied to the thickness distinction circuit 7 for comparison with a lower limit reference value (lower limit threshold) and an upper limit reference value (upper limit threshold) with respect to the thickness, and this distinction circuit 7 discriminates the filter tow as defective when the clamped image signal is equal to or lower than the lower limit threshold or equal to or more than the upper limit threshold.

Moreover, in order to discriminate suitability of the width of the filter tow 1, as in the construction shown in the above-mentioned FIG. 4, the signal (clamped image signal) of a predetermined scanning line (for example, a Z-th scanning line across the black zone), which is generated from the clamping circuit 5b and is obtained from scanning the black zone 3a of the background plate 3 is supplied to (1) an extraction circuit comprising a noise-eliminating circuit 6a and a slicing circuit 17, (2) an AND circuit 18 to which a clock signal (pulse signal) from the clock-generating circuit 19 is supplied, (3) a counter circuit 20 and (4) a width distinction circuit 21 for discriminating suitability of the width of the filter tow by comparison with reference values with respect to the width of the assembled fiber band. This distinction circuit supplies an announcing signal to an announcing circuit 22 for announcing that an abnormality or defect has occurred in the width of the filter tow when the count value from the counter circuit 20 is equal to or lower than the lower limit reference value (lower limit threshold) or equal to or more than the upper limit reference value (upper limit threshold) with respect to the width of the filter tow.

Furthermore, a signal (clamped image signal) of a scanning line, which is generated from the clamping circuit 5b and is obtained from scanning the white region 3b of the background plate 3 is supplied to a detecting means similar to that of the above-mentioned FIG. 7 for detection of the stain of the filter tow 1. Namely, the clamped image signals of scanning lines from the clamping circuit 5b are supplied to (1) an extraction circuit which comprises a differentiating circuit 26 as a noise-eliminating circuit, a comparing circuit 27, and an AND circuit 29, (2) a high level stain comparing circuit (first comparing circuit) 27, a first AND circuit 29 and a first stain counter circuit 31 to which a tow width window gate signal is supplied from the stain window gate circuit 36, and (3) a low level stain comparing circuit (second comparing circuit) 28, a second AND circuit 30 and a second stain counter circuit 32 to which a tow width window gate signal is supplied from the stain window gate circuit 36; then (4) a stain distinction circuit 33 compares the count signal (signal with respect to the count data) from the first counter circuit 31 with a predetermined reference value with respect to a stain of the assembled fiber band in order to discriminate suitability or acceptability of the stain. When the degree (count number) of the stain is equal to or more than the predetermined reference value, the stain distinction circuit supplies an announcing signal to an announcing circuit 34. The count values accumulated in the first stain counter circuit 31 and the second stain counter circuit 32 are reset to zero by the resetting circuit 35 in response to a timing signal from the timing circuit 10.

In response to various signals from the sync-separating circuit 5a, the timing circuit 10 supplies various necessary timing signals to the stain window gate circuit 36, the thickness trigger circuit 44, the width trigger circuit 45, the stain trigger circuit 46, and the resetting circuit 35.

In interlace scanning, the timing circuit 10 includes a frame/field conversion circuit, an image region gate circuit for the field, and an image region gate circuit in one scanning line, and generates various control signals within the auto distinction system of the present invention. The frame/field conversion circuit is a circuit for converting a video signal into a field signal. The video signal is formed from an odd-number field and an even-number field in one frame, and the field signal is a signal without having any concept of frame, odd number and even number. The image region gate circuit in the field is a gate circuit for eliminating scanning lines which are included in one field and to which neither vertical synchronizing signals nor image signals for synchronization with a receiver have been added. Moreover, the image region gate circuit in one scanning line is a gate circuit for eliminating regions (the horizontal synchronizing region, the front porch region, and the back porch region, etc.) other than the image signal included in one scanning line.

Such a system realizes distinction of suitability of the filter tow regardless of crimping of the filter tow, by efficient extraction of a plurality of characteristics with high accuracy. For example, in the case of a filter tow before being crimped, by using permeating illumination for illuminating the filter tow from the backside by an illuminating means, the suitability of both width and evenness in thickness of the tow can be discriminated. Moreover, in the case of the filter tow after being crimped, by using a background plate having the above-mentioned high contrast zones formed in a low contrast region, the suitability of both width and stain of the filter tow can be discriminated.

In the present invention, the illumination unit is not always necessary, however, the illumination unit is useful for increasing the imaging contrast of the imaging means and the accuracy of detection of the defects of the assembled fiber band. The illuminating means may be disposed at a position outside of visual field (or out-of-view) of the imaging means so as to illuminate the assembled fiber band, and the position where the illuminating means is disposed can be arbitrarily selected. For example, the assembled fiber band may be illuminated from the front side and/or the back side (for example, both front and back sides) of the assembled fiber band, and the illuminating means may illuminate the assembled fiber band by permeation of light beams through the assembled fiber band. For example, in the example shown in FIG. 1 to FIG. 3, the explanation is given by using the illumination unit 4 which illuminates the filter tow 1 from the back side, however, it is also possible that the illumination unit 4 is set on the foreside of the filter tow 1. Moreover, the filter tow may be also illuminated from both front and back sides of the filter tow by illumination units. Incidentally, a thickness defective portion of the assembled fiber band is usually detected by illuminating the assembled fiber band from the backside to the imaging means and using light permeating through the assembled fiber band.

The background plate is not always necessary, either. The color and brightness of the background plate may be selected according to the type and color of the assembled fiber band or detection items, and the color of the background plate may be different in brightness and contrast from that of the assembled fiber band, or may have a brightness equivalent to or a color similar to that of the assembled fiber band (or may be a low-contrast color to that of the assembled fiber band). For example, for the characteristic information with respect to the thickness, the background plate 3a is not limited to the black background plate 3a described in the above-mentioned FIG. 1 to FIG. 3, and may be a color similar to that of the filter tow 1 (for example, a color having an equivalent brightness, or white). Incidentally, the background plate is usually formed to be larger than the moving width of the assembled fiber band. Moreover, in the case where a plurality of characteristics (width, thickness, and other characteristics) are detected or discriminated in the moving assembled fiber band, the background plate advantageously has a region (a similar color region, etc.) similar to the assembled fiber band (the above-mentioned assembled fiber band or the like) in brightness, or has a region low in contrast (a low contrast region). Further, the background plate forms high contrast zones (band-shaped regions such as black regions) in the direction across the moving direction of the assembled fiber band by using the high contrast zones, the width of the assembled fiber band can be effectively detected.

Furthermore, in order to increase the detection efficiency of a defective portion from the assembled fiber band which continuously moves, if necessary, a filter (color filter or the like) may be interposed between the assembled fiber band and the imaging means or a filter may be attached to the imaging means. For example, a color filter may be used to detect a colored defective portion.

As an imaging means, various means which generate video signals can be employed, and the video signal may be a color video signal or a monochrome video signal as long as the video signal contains a luminance signal. Incidentally, the color video signal (including a full color video signal) may be used upon eliminating color signals (or chromatic signals) by a filter circuit. As such an imaging means, for example, a digital camera (motion picture camera) which can generate video signals is available as well as a video camera (monochrome or color video camera). That is, the imaging means is not limited to a video camera, and may be a digital type imaging means (a digital camera, etc., which can image a motion picture) as long as the imaging means can image an assembled fiber band which continuously moves and can generate a video signal.

An image (video) signal (NTSC video signal) from the imaging means comprises synchronizing signals for timing, a luminance signal showing the brightness of a picture, and color signals which are superposed on the luminance signal and express colors. In such a video signal (image signal), the luminance signal may be separated by using a separation circuit such as a filter, and may be used for detection of the characteristic information and/or extraction of the defect information.

Incidentally, in the above-mentioned example, the explanation is given by using a predetermined scanning line, however, it is also possible that the characteristic information is detected by using a plurality or all of the scanning lines including the image signal or it is possible to discriminate suitability of the defect information (information on at least one selected from a thickness, a width, and a stain).

Moreover, a stain usually comes out across a plurality of scanning lines, and therefore, by discriminating whether or not the count number is a predetermined number by the stain distinction circuit 33 based on the characteristic information (or defect information) from the plurality of scanning lines (in particular, scanning lines adjacent or in proximity to each other), erroneous detection due to instantaneous noise (or minute stain) can be prevented. For example, a circuit with the electrical construction shown in FIG. 7 (except for the announcing circuit) is formed corresponding to each of the plurality of scanning lines (in particular, scanning lines adjacent or in proximity to each other) including the characteristic information with respect to the stain. Further, a circuit is formed which comprises an AND circuit interposed between the plurality of stain distinction circuits 33 for each of the scanning lines and the single announcing circuit 34. Then, according to the flow of FIG. 9, for the characteristic information of the respective scanning lines, binarized signals are counted in Step S45, and it is discriminated whether or not the count signals (count data) are within or without the reference value range in Step S46, and when the count data becomes outside of the reference value range in Step S46, the count signals (or count data) corresponding to each of the scanning lines are supplied to the AND circuit, and a signal from the AND circuit is supplied to the announcing circuit 34. In this example, the distinction circuit comprises a plurality of stain distinction circuits 33 and the AND circuit. In this process, by using the distinction circuit comprising a plurality of stain distinction circuits 33 and the AND circuit, stain count signals are extracted from a plurality of scanning lines, and in the case where stain count signals have been extracted from each of the scanning lines, a stain is discriminated, so that stains can be detected with higher accuracy while effectively preventing erroneous detection.

Furthermore, even when a stain information (stain defect information, count signals) is detected from each of the scanning lines adjacent or in proximity to each other, in some cases, it cannot be discriminated whether the stain information is derived from one stain or a plurality of stains. Therefore, when the stain information (stain defect information, stain count signals) is detected from the respective scanning lines adjacent or in proximity to each other, it can be discriminated whether the stain is singular or plural by determining whether or not the stain count signals in the horizontal direction of the scanning lines adjacent or in proximity to each other are at the same position. For example, with respect to a moving assembled fiber band, since a stain information spans a plurality of scanning lines in many cases, when the stain signals are detected at the same position in the horizontal direction of the scanning lines adjacent or in proximity to each other, the stain may be discriminated as a single stain.

A video signal may be a signal of interlace scanning or may be a signal of non-interlace scanning. An extracting means for extracting defects or abnormal signals of the assembled fiber band from a clamped scanning signal (clamped image signal) is not particularly limited to a specific one, and may comprise various noise elimination means, for example, according to the type of a defect or an abnormal characteristic, the extracting means may comprise a differentiating means, an integration means, a means for comparison with thresholds, a waveform shaping means, and a slicing means by using thresholds, or may be formed by a combination of these means.

Moreover, in the above-mentioned example, a large stain and a latent stain are detected in stain detection. However, it is not necessary to detect a latent stain, and at least a stain except for latent stains may be detected. In the signal with respect to a stain, a signal with respect to the degree of stain and a signal with respect to the size of a stain region are contained. Therefore, by using a combination of the differentiating circuit and the counter circuit and others, a signal with respect to a stain may be separated into a signal with respect to the degree of the stain and a signal with respect to a stain range, and the stain may be discriminated in the distinction circuit based on each of the signals. In addition, each of the signals may be accumulated (or added) and multiplied, and the stain may be discriminated by the distinction circuit. Furthermore, in the above-mentioned example, defect(s) with respect to the thickness, width and/or stain of the assembled fiber band are detected, however, at least one characteristic of defective portion may be discriminated. Furthermore, in the distinction means, it is also possible to discriminate quality of the assembled fiber band by multiplying the respective defective characteristics (thickness, width, and stain) by a weighting factor.

The announcing means is not always necessary, however, in many cases, an announcing means (for example, light emission and sound generation means such as a buzzer) is provided for an announcing abnormal information on the basis of this distinction signal when the distinction signal from the distinction means becomes outside of a reference value with respect to the abnormal information.

The present invention is effective for quality control as well as non-defective or defective distinction of an assembled fiber band which is continuously manufactured. That is, in the present invention, the assembled fiber band is not particularly limited to a specific one as long as it can continuously move. The assembled fiber band usually comprises yarns or strands formed by bundling a plurality of filaments (for example, about 100 to 10000 filaments, in particular, about 250 to 5000 filaments). The assembled fiber band may have a two-dimensional spreading form, for example, a band-shaped assembled fiber band or a bandage-shaped assembled fiber band. The assembled fiber band may be a band-shaped or strip-shaped assembled fiber band comprising a plurality of yarns or strands, for example, a band-shaped assembled fiber band (band-shaped tow band) comprising a plurality of yarns which are bundled and adjacently arrayed each other, or a band-shaped assembled fiber band comprising a tow band (for example, a filter tow (cigarette or tobacco filter tow, etc.) and the like) in which yarns are adjacently arrayed each other and overlapped into a plurality of layers. Yarns or strands adjacently arrayed each other may overlap one another, and in the band-shaped body in which the yarns or strands are overlapped into a plurality of layers, the yarns or strands may be overlapped at the same position in the width direction, or may be overlapped each other while shifting their positions. For extracting or detecting a defective portion of the assembled fiber band by using permeating light, the assembled fiber band may be a light transmittable assembled fiber band such as the filter tow (cigarette or tobacco filter tow or the like). Furthermore, the assembled fiber band such as tow may comprise non-crimped filaments (or non-crimped yarns or tow), or may comprise crimped filaments (or crimped yarns or tow). The present invention is effective for quality control, etc., in the manufacturing process of a filter tow for a cigarette or tobacco.

Incidentally, the moving speed of the assembled fiber band is not particularly limited to a specific one, and may be, for example, about 0.1 to 100 m/sec, and preferably about 1 to 50 m/sec (for example, 5 to 30 m/sec).

In the assembled fiber band, the degrees of proximity and overlapping of yarns adjacent to each other fluctuate depending on moving of the yarns, and thickness and fiber density (filamentation state) easily fluctuate. In the present invention, even in the case of an assembled fiber band which moves at a high speed (non-crimped or crimped band-shaped filter tow, etc., made of a plurality of yarns), various defective portions (the defect information with respect to at least one characteristic selected from the width, the thickness, and the stain) can be extracted or detected with high accuracy by detection or extracting means. Therefore, the present invention is useful for quality control of the assembled fiber band in the manufacturing and processing. Incidentally, in many cases of an assembled fiber band (filter tow, etc., before being crimped) made of non-crimped filament (or non-crimped yarns or tow), a characteristic information with respect to at least one of the thickness the width, and the stain is detected, and in most cases of an assembled fiber band (filter tow, etc., after being crimped) made of crimped filament (or crimped yarns or tow), the characteristic information with respect to at least one characteristic of the width and stain is detected.

For example, in manufacturing of a crimped assembled fiber band (crimped filter tow, etc.), since overlapping states (evenness in thickness) of yarns (or bands) before and after being crimped can be discriminated, the discriminated state is effectively used for quality control of the assembled fiber band. Furthermore, defective portions (thickness uneven portions, etc.,) of the assembled fiber band which cannot be detected by visual check during moving can be extracted or detected. Further, it can be discriminated whether or not the overlapping state (thickness evenness) of yarns (or bands) before being crimped is the same as the initially set state, or whether or not the overlapping state is in an allowable range. Therefore, by using the thickness evenness as an index, the yarns (or bands) can be supplied for the crimping process while the yarns (or bands) are overlapped with predetermined evenness, whereby the entirety of the assembled fiber band can be crimped evenly. Furthermore, by controlling the width of the assembled fiber band, it can also be discriminated whether or not the center of the tow band before being crimped deviates from the center of a crimper. Therefore, the whole assembled fiber band can be evenly crimped by supplying the position (or placement) of the center axis of the tow band to the crimper as an index. Furthermore, by detecting stains of the assembled fiber band, finished products can be effectively prevented from mixture of stained portions.

In the present invention, a transmitting means or transfer means supplies at least one of characteristic information selected from a width count data, a thickness clamped image signal, and a stain count data to a process controlling computer, so that the characteristic information can be used as a time sequence or time-series fluctuation information and can be effectively used for process control in the manufacturing process of the assembled fiber band and quality control of the assembled fiber band. As described above the transmitting means or transfer means usually comprises an interface means (interface circuit) for transmitting or transferring at least one of characteristic information selected from the width count data, the thickness clamped image signal, and the stain count data, and a trigger means (trigger circuit) which generates a trigger signal for transmitting or transferring the characteristic information to the computer via this interface means. The trigger signal is used for announcing the transferring timing of the characteristic information to the computer.

Figure 13:
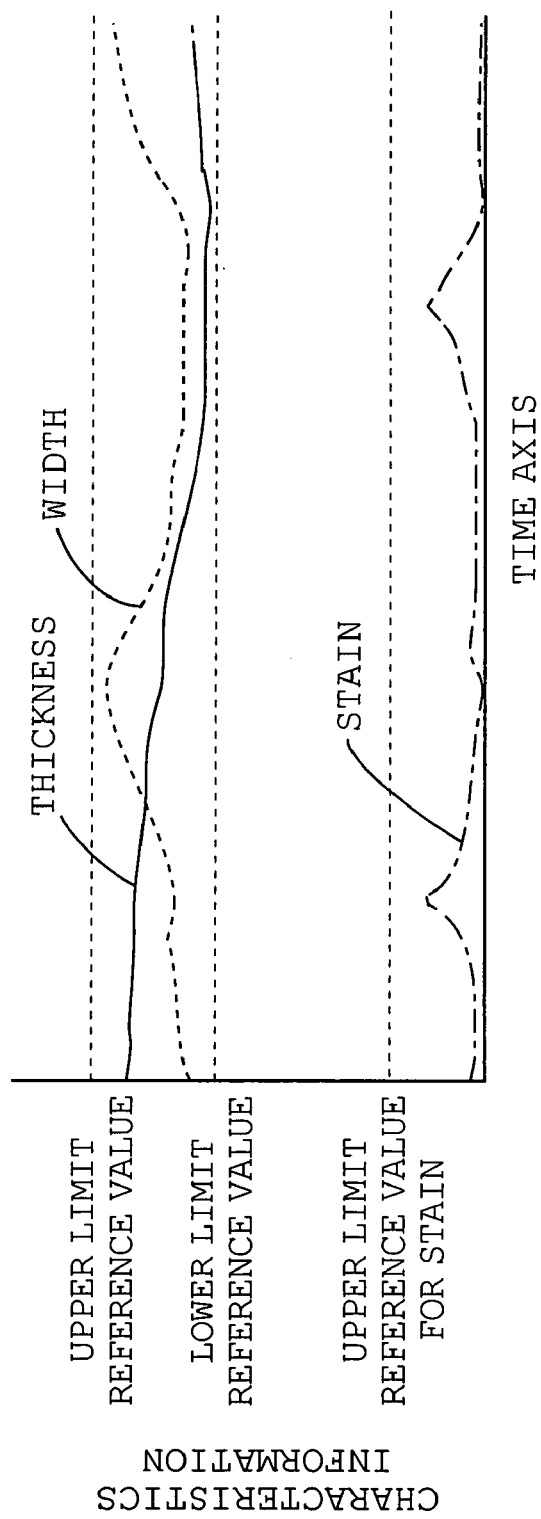
FIG. 13 is a graph showing time sequence fluctuations of a characteristic information of a cigarette filter tow which continuously moves or runs.
Figure 14:
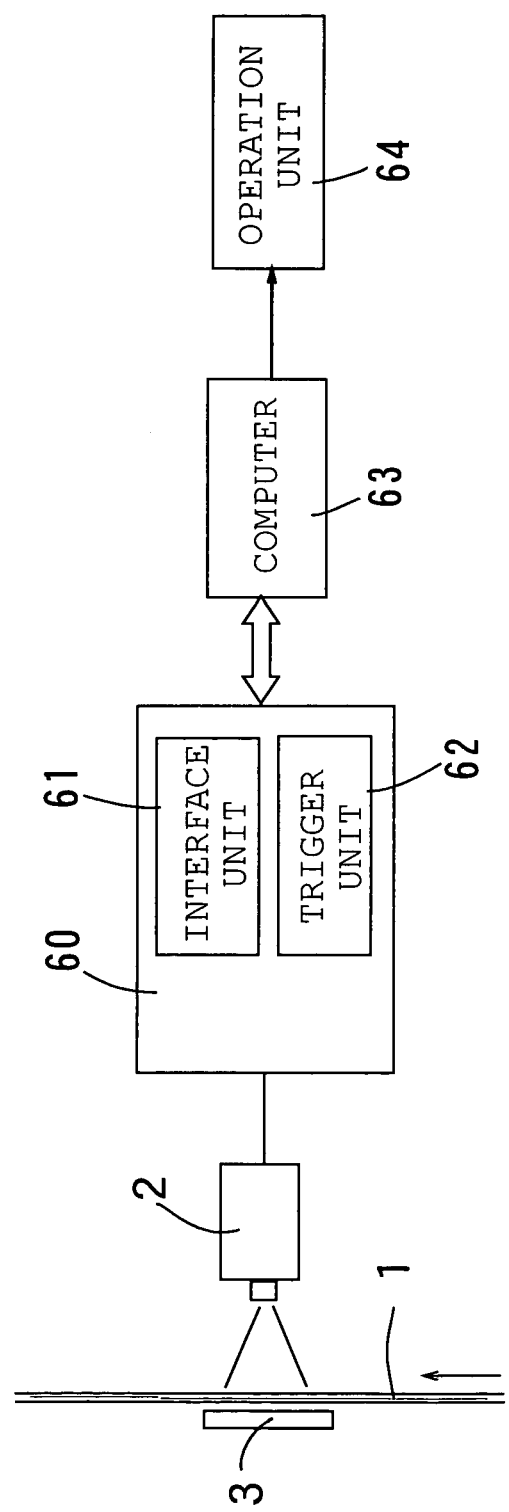
FIG. 14 is a block diagram showing an example of process control using the auto distinction system of the present invention.

FIG. 13 is a graph showing time sequence fluctuations of the characteristic information of a cigarette filter tow which continuously moves, and FIG. 14 is a block diagram showing an example of process control using the auto distinction system of the present invention.

As shown in FIG. 13, the characteristics with respect to width, thickness, and stain of a continuously moving filter tow (band-shaped tow) fluctuate with time. For example, the width of the filter tow becomes narrower or wider with time, the thickness of the filter tow also becomes thicker or thinner in time series, and the stains of the filter tow increase or decrease with time. From these information, the defect information is extracted, and when the extracted signal becomes outside of the reference value, an abnormality or defect is announced by an announcing means, and the portion or lot corresponding to the defect information of the filter tow are discriminated as defective. Therefore, the manufacturing operation rate and yield of the filter tow lower, and the planned production volume cannot be achieved, and at last, the manufacturing costs increase. On the other hand, the values of various characteristic information fluctuate within the thresholds (between the lower limit reference value and the upper limit reference value) even when the auto distinction system does not discriminate the values as defective, and the fluctuation information (time sequence fluctuation information) includes useful information.

In FIG. 14, the filter tow 1 which moves on the foreside of the background plate 3 is imaged by a video camera 2, and a video signal is transmitted to an auto distinction system 60, and in this system, the defect information is extracted from the information with respect to at least one characteristic selected from a width, a thickness, and a stain as described above, and it is discriminated whether or not the extracted signal becomes outside of the reference values (the lower limit reference value and the upper limit reference value) by a distinction means. When a distinction signal becomes outside of reference values with respect to a defect information, based on this distinction signal, the defect information is announced as an abnormality.

On the other hand, even when the defect information does not include an abnormality, the time-series characteristic information (fluctuation data) is data-transmitted to the computer 63 by the transmission or transfer means (transfer means comprising an interface unit (interface circuit) 61 and a trigger unit (trigger circuit) 62) inside the auto distinction system 60. In the computer 63, trend analysis with respect to various characteristic information is carried out based on the fluctuation data. According to the obtained trend, by using the correlation between the control target and the control amount obtained from factor analysis, process control can be conducted by automatically or manually operating the control target with the operation unit 64 in a production equipment. For example, even when the data value of the characteristic information (characteristic information on the thickness or width) is within the range between the lower limit reference value and the upper limit reference value, process control can be consistently made to maintain the data value of the characteristic information at the central reference value between the lower limit reference value and the upper limit reference value.

By using a system comprising the auto distinction system and a separate computer (process controlling computer), occurrence of abnormal products or defective products can be prevented by process control, and quality control of the filter tow can be effectively performed. Furthermore, at least one characteristic information (processing condition) selected from the width, the thickness, and the stain of the filter tow (band-shaped tow) can be monitored in real time on the computer. According to the time sequence trend of the characteristic information, a subsequent condition can be estimated based on the time sequence trend of the characteristic information. Therefore, before the time sequence fluctuation value becomes outside of the lower limit reference value and the upper limit reference value, occurrence of defective products can be prevented by operating the operation unit of the production equipment.

Incidentally, at least one of information selected from the count data with respect to the width, the clamped image signal with respect to the thickness, and the count data with respect to the stain may be transmitted or transferred to the computer, or a plurality of characteristic information (characteristic information of the width and thickness, the width and stain, the thickness and stain, or the width, thickness, and stain) may be transmitted or transferred to the computer. The characteristic information to be transmitted or transferred to the computer may be a defect information. The characteristic information may be utilized as a time sequence fluctuation information (time series fluctuation information) by being transmitted or transferred to the computer one by one, and if necessary, stored in a storage circuit of the computer. The characteristic information may be used as a time sequence fluctuation information by being stored in the storage circuit of the distinction system for each predetermined scanning line, and being transmitted or transferred a plurality of stored information to the computer. In the case where at least one piece of the characteristic information selected from the count data with respect to the width, the clamped image signal with respect to the thickness, and the count data with respect to the stain is used as a fluctuation information (time series fluctuation information) in the computer, all of the characteristic information contained in the predetermined scanning lines (for example, single or a plurality of scanning lines or all the scanning lines in one field) may be supplied to the computer, or the characteristic information of predetermined scanning lines may be averaged and supplied to the computer. Moreover, the characteristic information of predetermined scanning lines may be transmitted or transferred to the computer at a predetermined time interval.

The interface circuit can employ various interfaces according to the characteristics of the characteristic information (in particular, depending on whether the information is analog or digital). For example, a buffer circuit or the like can be used for digital signals such as the width count data, the stain count data, and the trigger signal, and an amplifier circuit or the like can be used for the clamped image signal (thickness clamped image signal or the like). The trigger circuit informs the transferring timing of the information (data or image signal) to the computer. Therefore, the characteristic information transmitted or transferred to the computer via the interface circuit is synchronized with the trigger signal from the trigger circuit and taken into the computer in a predetermined timing.

Incidentally, the distinction system may have an analog/digital (A/D) conversion circuit to transmit or transfer the characteristic information (characteristic image signal) to the computer as a digital signal. The computer may have an analog/digital (A/D) conversion circuit to take-in the characteristic information (characteristic image signal) from the distinction system as a digital signal.

INDUSTRIAL APPLICABILITY

In the present invention, since a characteristic information (defect information) of an assembled fiber band can be efficiently extracted, even in a continuously moving assembled fiber band, the quality of the assembled fiber band can be accurately discriminated by precisely extracting defective portions or uneven portions of the assembled fiber band. Moreover the present invention ensures not only detection of a single characteristic of the assembled fiber band, but also discriminating a defect information with respect to at least two characteristics selected from a width, a thickness, and a stain. Furthermore, even in the case of a band-shaped assembled fiber band such as filter tow which moves at a high speed, fluctuations in width and thickness and stains can be efficiently detected. Furthermore, not only can defective portions be detected by the system by itself, but also the characteristic information is supplied to a computer (for example, a process controlling computer) and analyzed by the computer as a time sequence fluctuation information, whereby the information can be used for process control and quality control at a production site (point of production).

The invention claimed is:

1. An auto distinction system for transmitting a characteristic information as time sequence fluctuation information to a computer, the characteristic information including a defect information, and corresponds to at least one characteristic selected from the group consisting of a width, a thickness, and a stain of an assembled fiber band which continuously moves; the system comprising:
   imaging means for imaging an assembled fiber band which continuously moves,
   sync-separating and clamping means for sync-separating and clamping a video signal from the imaging means,
   detecting means for detecting a characteristic information including a defect information, with respect to at least one characteristic selected from the group consisting of a width, a thickness, and a stain of the assembled fiber band on the basis of a clamped image signal from the sync-separating and clamping means,
   extracting means for extracting the defect information from the characteristic information detected by the detecting means, and
   distinction means for discriminating suitability of the extracted information based on an extracted signal from the extracting means and a reference signal with respect to the characteristic or defect information,
   wherein at least one characteristic information selected from the group consisting of a width count data, a thickness clamped image signal, and a stain count data is transmitting to the computer.

2. The auto distinction system according to claim 1, wherein the auto distinction system is free from a memory for storing a convened digital signal from the clamped image signal, and the characteristic information is supplied to the computer as a digital data.

3. The auto distinction system according to claim 1, wherein the clamped image signal is a clamped image signal of a predetermined scanning line across an imaging region or field, and the characteristic information including the time sequence fluctuating defect information is detected by the detecting means.

4. The auto distinction system according to claim 1, wherein the sync-separating and clamping means sync-separates and clamps a luminance signal in the video signal.

5. The auto distinction system according to claim 1, which comprises an extracting means for extracting a low frequency signal from the clamped image signal, and a distinction means for discriminating an amplitude width of the low frequency signal being within or without reference value range.

6. The auto distinction system according to claim 1, which comprises an extracting means for extracting the thickness clamped image signal from the clamped image signal at least by a high-frequency-noise-eliminating means, and a distinction means for discriminating an amplitude width of the thickness clamped image being within or without reference value range.

7. The auto distinction system according to claim 1, wherein the assembled fiber band comprises a plurality of yarns each of which is bundled and is adjacently arrayed each other.

8. The auto distinction system according to claim 1, wherein the assembled fiber band comprises a tow band in which yams are adjacently arrayed each other and the arrayed yams are overlapped into a plurality of layers.

9. The auto distinction system according to claim 1, further comprising
   illuminating means which is disposed outside of a visual field of the imaging means and illuminates the assembled fiber band, and
   a background plate for forming the background against the assembled fiber band relative to the illuminating means.

10. The auto distinction system according to claim 9, wherein the background plate has a high contrast color to the color of the assembled fiber band, and the extracting means extracts the defect information with respect to at least one characteristic selected from the group consisting of a width and a thickness of the assembled fiber band by using scanning lines of a video signal obtained from scanning the high contrast color region.

11. The auto distinction system according to claim 9, wherein the background plate has a color being similar or low-contrast against the color of the assembled fiber band, and the extracting means extracts the defect information with respect to at least one characteristic selected from the group consisting of a stain and a thickness of the assembled fiber band by means of scanning lines of a video signal obtained from scanning the similar or low contrast color region.

12. The auto distinction system according to claim 9, wherein the assembled fiber band comprises a light transmittable band-shaped assembled fiber band, the background plate is larger than the moving width of the band-shaped assembled fiber band and has a color region being similar or low-contrast to the color of the band-shaped assembled fiber band, and the background plate forms high contrast zones crossing the moving direction of the assembled fiber band.

13. The auto distinction system according to claim 1, further comprising:
   announcing means wherein
   in the case where a distinction signal from the distinction means is out of a reference value with respect to defect information, the announcing means announces the defect information based on the distinction signal.

14. The auto distinction system according to claim 1, wherein the assembled fiber band is a filter tow, and the extracting means extracts defect information with respect to at least two characteristics selected from the group consisting of a width, a thickness, and a stain of the assembled fiber band.

15. The auto distinction system according to claim 1, comprising
   (a) sync-separating means for separating sync signals from the video signal from the imaging means;
   (b) clamping means for clamping the video signal in response to the sync signals from the sync-separating means;
   (c-1) extracting means for extracting a thickness defect signal from the clamped image signal with respect to thickness of the assembled fiber band, and (c-2) thickness distinction means for discriminating suitability of the thickness by comparing the extracted defect signal with a reference value with respect to thickness of the assembled fiber band;
   (d-1) extracting means for extracting a width signal from the clamped image signal with respect to width of the assembled fiber band, and (d-2) width distinction means for discriminating suitability of the width by comparing the extracted width signal with a reference value with respect to width of the assembled fiber band; and
   (e-1) extracting means for extracting a stain signal from the clamped image signal with respect to a stain of the assembled fiber band, and (e-2) stain distinction means for discriminating suitability of the stain by comparing the extracted stain signal with a reference value with respect to a stain of the assembled fiber band.

16. The auto distinction system according to claim 15, comprising
   (a) thickness distinction means which eliminates at least high frequency noise from the clamped image signal of the assembled fiber band, and discriminates suitability of the thickness by comparing the noise-eliminated clamped image signal with a reference value with respect to a thickness of the assembled fiber band,
   (b-1) extracting means which eliminates noise from a clamped image signal of the assembled fiber band, and generates a rectangular signal corresponding to the width of the assembled fiber band, (b-2) counter means for counting rectangular portions of the clamped image signal by a clock means, and (b-3) width distinction means for discriminating suitability of the width by comparing the count data of the counter means with a reference value with respect to a width of the assembled fiber band, and
   (c-1) differentiating means for differentiating a clamped image signal of the assembled fiber band, (c-2) comparing means for discriminating a large stain by comparing the differentiated clamped image signal and a reference value with respect to a stain of the assembled fiber band, and (c-3) counter means for counting the number of stains on the basis of the defect information and the image-width information, in which the defect information relates to the stain from the comparing means and the image-width information relates to the image width from the imaging means, and (c-4) stain distinction means for discriminating suitability of the stain by comparing the count data counted by the counter means with a reference value with respect to a stain of the assembled fiber band.

17. The auto distinction system according to claim 16, wherein the comparing means comprises first comparing means for discriminating a larger stain of the assembled fiber band by comparing the differentiated clamped image signal with a first reference value with respect to stain largeness, and second comparing means for discriminating a smaller stain of the assembled fiber band by comparing the differentiated clamped image signal with a second reference value with respect to stain smallness;
   the counter means comprises first counter means for counting the number of large stains on the basis of both the defect information with respect to the stain from the first comparing means and the image width information from the imaging means, and second counter means for counting the number of small stains on the basis of both the defect information with respect to the stain from the second comparing means and the image width information from the imaging means; and the stain distinction means discriminates acceptability of the stain by comparing the count data counted by the first counter means and a reference value with respect to a large stain of the assembled fiber band.

18. The auto distinction system according to claim 1, wherein the extracting means extracts defect information with respect to at least one characteristic selected from the group consisting of a width, a thickness, and a stain of a crimped or non-crimped band-shaped filter tow which continuously moves and comprises a plurality of yarns.

19. The auto distinction system according to claim 1, further comprising:

transmitting means for supplying at least one piece of characteristic information selected from the group consisting of a width count data, a thickness clamped image signal, and a stain count data to a process controlling computer.

20. The auto distinction system according to claim 19, wherein the transmitting means comprises interface means for transmitting or transferring at least one piece of characteristic information selected from the group consisting of the width count data, the thickness clamped image signal, and the stain count data, and trigger means for generating a trigger signal for adjusting the transferring timing of the characteristic information to the computer via the interface means.

21. An auto distinction method for transmitting a characteristic information as time sequence fluctuation information to a computer, the characteristic information including a defect information, and corresponds to at least one characteristic selected from the group consisting of a width, a thickness, and a stain of an assembled fiber band which continuously moves; wherein the method comprising:

imaging a continuously moving assembled fiber band by imaging means, sync-separating and clamping a video signal from the imaging means, detecting a characteristic information containing a defect information with respect to at least one characteristic selected from the group consisting of a width, a thickness, and a stain of the assembled fiber band based on a clamped image signal, extracting a defect information with respect to the above-mentioned characteristic from the detected characteristic information, and discriminating suitability of the defect information based on the extracted signal and a reference signal with respect to the defect information; and at least one characteristic information selected from the group consisting of a width count data, a thickness clamped image signal, and a stain count data is transmitting to the computer.

22. An auto distinction system for transmitting a characteristic information as time sequence fluctuation information to a computer, the characteristic information including a defect information, and corresponds to at least one characteristic selected from the group consisting of a width, a thickness, and a stain of an assembled fiber band which continuously moves; the system comprising:

imaging means for imaging an assembled fiber band which continuously moves, sync-separating and clamping means for sync-separating and clamping a video signal from the imaging means, detecting means for detecting a characteristic information including a defect information, with respect to at least one characteristic selected from the group consisting of a width, a thickness, and a stain of the assembled fiber band on the basis of a clamped image signal from the sync-separating and clamping means, extracting means for extracting the defect information from the characteristic information detected by the detecting means, and distinction means for discriminating suitability of the extracted information based on an extracted signal from the extracting means and a reference signal with respect to the characteristic or defect information, wherein at least one characteristic information selected from the group consisting of a width count data, a thickness clamped image signal, and a stain count data is transmittable to the computer, and wherein the auto distinction system is free from a memory for storing a converted digital signal from the clamped image signal, and the characteristic information is supplied to the computer as a digital data.

* * * * *